United States Patent
Diller et al.

(10) Patent No.: US 11,850,184 B2
(45) Date of Patent: *Dec. 26, 2023

(54) ALTERING TEMPERATURE IN A MAMMALIAN BODY

(71) Applicant: Board of Regents, The University of Texas System, Austin, TX (US)

(72) Inventors: Kenneth R. Diller, Elgin, TX (US); Daniel W. Hensley, Austin, TX (US); Timothy T. Diller, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 68 days.

This patent is subject to a terminal disclaimer.

(21) Appl. No.: 17/349,540

(22) Filed: Jun. 16, 2021

(65) Prior Publication Data
US 2021/0307960 A1 Oct. 7, 2021

Related U.S. Application Data

(63) Continuation of application No. 15/377,644, filed on Dec. 13, 2016, now abandoned, which is a (Continued)

(51) Int. Cl.
*A61F 7/08* (2006.01)
*A61F 7/00* (2006.01)
(Continued)

(52) U.S. Cl.
CPC ............. *A61F 7/08* (2013.01); *A61F 7/00* (2013.01); *A61F 7/03* (2013.01);
(Continued)

(58) Field of Classification Search
CPC ...... A61F 2007/0036; A61F 2007/0045; A61F 2007/0047; A61F 7/02; A61F 7/10
See application file for complete search history.

(56) References Cited

U.S. PATENT DOCUMENTS

| 4,987,896 A | 1/1991 | Nakamatsu |
| 5,018,521 A | 5/1991 | Campbell |

(Continued)

FOREIGN PATENT DOCUMENTS

| DE | 202006020386 | 8/2008 |
| EP | 1028679 | 7/2003 |

(Continued)

OTHER PUBLICATIONS

Bergersen, T.K., et al., "Local constriction of arteriovenous anastomoses in the cooled finger," Am J . Physiol. Regulatory Integrative Comp. Physiol., 273:R880-R886 (1997).

(Continued)

*Primary Examiner* — Kaitlyn E Smith
(74) *Attorney, Agent, or Firm* — Meunier Carlin & Curfman LLC

(57) ABSTRACT

The present application relates to systems and methods for altering temperature in a mammalian body. Optionally, the systems and methods can be used to lower or raise core body temperature of a mammalian subject. Optionally, the systems and methods can be used to lower or raise the temperature of glabrous skin of a mammalian subject.

3 Claims, 20 Drawing Sheets

US 11,850,184 B2

Page 2

Related U.S. Application Data continuation of application No. 14/143,436, filed on Dec. 30, 2013, now Pat. No. 9,549,844, which is a continuation of application No. 12/881,767, filed on Sep. 14, 2010, now Pat. No. 8,617,230.

(60) Provisional application No. 61/276,787, filed on Sep. 16, 2009, provisional application No. 61/276,764, filed on Sep. 16, 2009.

(51) Int. Cl.
*A61F 7/03* (2006.01)
*A61F 7/02* (2006.01)
*A61N 7/00* (2006.01)
*A61N 5/06* (2006.01)
*A61N 5/10* (2006.01)

(52) U.S. Cl.
CPC ........... *A61F 2007/0011* (2013.01); *A61F 2007/0024* (2013.01); *A61F 2007/0036* (2013.01); *A61F 2007/0045* (2013.01); *A61F 2007/0054* (2013.01); *A61F 2007/0056* (2013.01); *A61F 2007/0071* (2013.01); *A61F 2007/0093* (2013.01); *A61F 2007/0225* (2013.01); *A61F 2007/0239* (2013.01); *A61N 5/0625* (2013.01); *A61N 5/1031* (2013.01); *A61N 7/00* (2013.01)

(56) References Cited

U.S. PATENT DOCUMENTS

| | | | |
|---|---|---|---|
| 5,269,369 A | 12/1993 | Faghri | |
| 5,409,500 A | 4/1995 | Dyrek | |
| 5,514,170 A | 5/1996 | Mauch | |
| 5,683,438 A | 11/1997 | Grahn | |
| 5,766,235 A | 6/1998 | Kostopoulo | |
| 5,879,315 A | 3/1999 | Mosley | |
| 5,913,886 A | 6/1999 | Soloman | |
| 5,921,243 A | 7/1999 | Shakoor | |
| 5,935,157 A | 8/1999 | Harmon | |
| 6,146,413 A | 11/2000 | Harman | |
| 6,149,674 A | 11/2000 | Borders | |
| 6,188,930 B1 | 2/2001 | Carson | |
| 6,264,681 B1 | 7/2001 | Usui | |
| 6,375,673 B1 | 4/2002 | Clifton et al. | |
| 6,375,674 B1 | 4/2002 | Carson | |
| 6,409,745 B1 | 6/2002 | Ducharme et al. | |
| 6,461,379 B1 | 10/2002 | Carson et al. | |
| 6,551,347 B1 | 4/2003 | Elkins | |
| 6,582,456 B1 | 6/2003 | Hand et al. | |
| 6,602,277 B2 | 8/2003 | Grahn et al. | |
| 6,620,187 B2 | 9/2003 | Carson et al. | |
| 6,648,905 B2 | 11/2003 | Hoglund | |
| 6,656,208 B2 | 12/2003 | Grahn et al. | |
| 6,660,027 B2 | 12/2003 | Gruszecki et al. | |
| 6,669,715 B2 | 12/2003 | Hoglund et al. | |
| 6,673,099 B2 | 1/2004 | Grahn et al. | |
| 6,685,731 B2 | 2/2004 | Kushnir et al. | |
| 6,692,518 B2 | 2/2004 | Carson | |
| 6,772,445 B2 | 8/2004 | Yeager | |
| 6,799,063 B2 | 9/2004 | Carson | |
| 6,802,855 B2 | 10/2004 | Ellingboe | |
| 6,818,012 B2 | 11/2004 | Ellingboe | |
| 6,827,728 B2 | 12/2004 | Ellingboe et al. | |
| 6,840,955 B2 | 1/2005 | Ein | |
| 6,846,322 B2 | 1/2005 | Kane et al. | |
| 6,893,455 B1 | 5/2005 | Rafferty et al. | |
| 6,902,574 B2 | 6/2005 | Graham et al. | |
| 6,921,198 B2 | 7/2005 | Gruszecki | |
| 6,966,922 B2 | 11/2005 | Grahn et al. | |
| 6,974,442 B2 | 12/2005 | Grahn et al. | |
| 7,044,960 B2 | 5/2006 | Voorhees et al. | |
| 7,056,334 B2 | 6/2006 | Lennox | |
| 7,089,995 B2 | 8/2006 | Koscheyev et al. | |
| 7,122,047 B2 | 10/2006 | Grahn et al. | |
| 7,160,316 B2 | 1/2007 | Hamilton | |
| 7,179,281 B2 | 2/2007 | Ferdinand | |
| 7,182,776 B2 | 2/2007 | Grahn et al. | |
| 7,351,252 B2 | 4/2008 | Altshuler et al. | |
| 7,361,186 B2 | 4/2008 | Voorhees et al. | |
| 7,785,359 B2 | 8/2010 | Latham | |
| 7,833,179 B2 | 11/2010 | Filtvedt et al. | |
| 7,862,600 B2 | 1/2011 | Grahn et al. | |
| 7,972,287 B2 | 7/2011 | Stewart et al. | |
| 8,066,752 B2 | 11/2011 | Hamilton et al. | |
| 8,182,521 B2 | 5/2012 | Kane et al. | |
| 8,287,581 B2 | 10/2012 | Grahn et al. | |
| 8,337,539 B2 | 12/2012 | Ting et al. | |
| 8,372,130 B2 | 2/2013 | Young | |
| 8,617,230 B2 * | 12/2013 | Diller ............... | A61F 7/00 607/108 |
| 8,808,343 B2 | 8/2014 | Koch | |
| 9,339,412 B2 * | 5/2016 | Diller ............... | A61F 7/00 |
| 9,549,844 B2 * | 1/2017 | Diller ............... | A61F 7/08 |
| 11,229,548 B2 * | 1/2022 | Diller ............... | A61F 7/0085 |
| 2002/0022871 A1 | 2/2002 | Grahn et al. | |
| 2002/0161419 A1 | 10/2002 | Carson et al. | |
| 2003/0024684 A1 | 2/2003 | Lyons | |
| 2003/0040783 A1 | 2/2003 | Salmon | |
| 2003/0109910 A1 | 6/2003 | Lachenbruch et al. | |
| 2003/0114903 A1 | 6/2003 | Ellingboe et al. | |
| 2003/0176904 A1 | 9/2003 | Patterson | |
| 2003/0208251 A1 | 11/2003 | Papay et al. | |
| 2004/0147989 A1 | 7/2004 | Terakita et al. | |
| 2004/0225341 A1 | 11/2004 | Schock et al. | |
| 2005/0060012 A1 | 3/2005 | Voorhees | |
| 2005/0209663 A1 | 9/2005 | Hamilton et al. | |
| 2006/0067994 A1 | 3/2006 | Purcell | |
| 2006/0111766 A1 | 5/2006 | Grahn et al. | |
| 2006/0144557 A1 | 7/2006 | Koscheyev et al. | |
| 2006/0190062 A1 | 8/2006 | Worthen | |
| 2007/0060987 A1 | 3/2007 | Grahn et al. | |
| 2007/0112400 A1 | 5/2007 | Hamilton et al. | |
| 2007/0123962 A1 | 5/2007 | Grahn et al. | |
| 2007/0162096 A1 | 7/2007 | Zakuto et al. | |
| 2007/0239237 A1 | 10/2007 | Choi et al. | |
| 2008/0021531 A1 | 1/2008 | Kane et al. | |
| 2008/0027523 A1 | 1/2008 | Behringer et al. | |
| 2008/0064992 A1 | 3/2008 | Stewart et al. | |
| 2008/0077205 A1 | 3/2008 | Cazzini | |
| 2008/0132816 A1 | 6/2008 | Kane et al. | |
| 2008/0132976 A1 | 6/2008 | Kane et al. | |
| 2008/0249593 A1 | 10/2008 | Cazzini et al. | |
| 2008/0255644 A1 | 10/2008 | Carson | |
| 2009/0036959 A1 | 2/2009 | Filtvedt et al. | |
| 2009/0048649 A1 | 2/2009 | Peret et al. | |
| 2009/0099629 A1 | 4/2009 | Carson et al. | |
| 2009/0131835 A1 | 5/2009 | Voorhees et al. | |
| 2009/0319009 A1 | 12/2009 | Koch et al. | |
| 2010/0106230 A1 | 4/2010 | Buchanan | |
| 2010/0145421 A1 | 6/2010 | Tomlinson et al. | |
| 2010/0191314 A1 | 7/2010 | Young | |
| 2011/0021960 A1 | 1/2011 | Filtvedt et al. | |
| 2011/0066217 A1 | 3/2011 | Diller et al. | |
| 2013/0152950 A1 | 6/2013 | Giap | |
| 2013/0317578 A1 | 11/2013 | Diller et al. | |
| 2014/0276253 A1 | 9/2014 | Varga et al. | |
| 2014/0276254 A1 | 9/2014 | Varga et al. | |
| 2014/0277301 A1 | 9/2014 | Varga et al. | |
| 2014/0350645 A1 | 11/2014 | Diller et al. | |
| 2016/0120691 A1 | 5/2016 | Kirwan et al. | |
| 2017/0049613 A1 | 2/2017 | Diller et al. | |

FOREIGN PATENT DOCUMENTS

| | | |
|---|---|---|
| GB | 1095988 | 12/1967 |
| WO | 1999/023980 | 5/1999 |
| WO | 2001/080790 | 11/2001 |
| WO | 2008/094485 | 8/2008 |
| WO | 2011/034852 | 3/2011 |

(56) References Cited

FOREIGN PATENT DOCUMENTS

| WO | 2013/074128 | 5/2013 |
|---|---|---|
| WO | 2013/102051 | 7/2013 |
| WO | 2013/102056 | 7/2013 |

OTHER PUBLICATIONS

Blix, A.S., et al., "Selective brain cooling and its vascular basis in diving seals," J. Exper. Biol, 213:2610-2616(2010).
Charkoudian, N., "Skin blood flow in adult human thermoregulation: how it works, when it does not, and why," Mayo Clin Proc., 78:603-612 (2003).
Chato, J.C., "Heat transfer to bloodvessels," J. Biomech. Engr., 102:110-118 (1980).
Clark, E.R., "Arterio-venous anastomoses," Physiol. Rev., 229-247 (1938).
Clifton, G.L., "Is keeping cool still hot? An update on hypothermia in brain injury," Curr. Opin. Crit. Care, 10:116-119 (2004).
Diller, K.R., et al., "Hypothermia Therapy for Brain Injury," Ann. Rev. Biomedical Engineering, 11:135-162 (2009).
Garner, G.B., et al., "Vacuum-assisted wound closure provides early fascial reapproximation in trauma patients with open abdomens," Amer. J. Surg., 182:630-638 (2001).
Grahn, D.A., et al., "Heat extraction through the palm of one hand improves aerobic exercise endurance in a hot environment," J. Appl. Physiol, 99:971-78 (2005).
Grahn, D.A., et al., "Heat loss through the glabrous skin surfaces of heavily insulated, heat-stressed individuals," J. Biomech. Engr. 131:071005.1-6 (2009).
Grahn, D.A., et al., "Recovery from mild hypothermia can be accelerated by mechanically distending blood vessels in the hand," J. Appl. Physiol, 85:1643-1648 (1998).
Hagobian, T.A., et al., "Foot cooling reduces exercise-induced hyperthermia in men with spinal cord injury," Med. Sci. Sports Exerc, 36:411-417 (2004).
Hales, J.R.S., et al., "Control of arteriovenous anastomoses, in Vasodilation: Vascular Smooth Muscle, Peptides, Autonomic Nerves and Endothelium," ed. PM Vanhoutte, Raven Press, New York, 321-332 (1988).
Hales, J.R.S., et al., "Thermal control of blood flow through capillaries and arteriovenous anastoses in skin of Sheep," Pflugers Archiv, 378:55-63 (1978).
Jessen, C., et al., "Balanced and unbalanced temperature signals generated in spinal cord of the ox," Am. J. Physiol, 222: 1343-1347 (1972).
Johnson, J.M., et al., "Cardiovascular adjustments to heat stress in Handbook of Physiology," Section 4: Environmental Physiology, vol. 1, Oxford University Press, New York, pp. 215-243 (1996).
Kräuchi, K., et al., "Warm feet promote the rapid onset of sleep," Nature, 401:36-37 (1999).
Kurz, A., et al., "Perioperative normothermia to reduce the incidence of surgical-wound infection and shorten hospitalization," N. Engl. J. Med., 334(19):1209-1215 (1996).
Manelli, A., et al., "Plexiform vascular structures in the human digital dermal layer: A SEM corrosion casting morphological study," Euro. J. Morphol., 42(4/5):173-177 (2005).
Markgraf, C.G., et al., "Treatment window for hypothermia in brain injury," J. Neruosurg, 95:979-983 (2001).

Roselli, R.J., et al., "Biotransport: Principles and Applications," Springer Press, New York, pp. 489-785 (2011).
Rowell, L.B., "Human cardiovascular adjustments to exercise and thermal stress," Physiol. Rev, 54:75-159(1974).
Sangiori, S., et al., "Microvascularization of the human digit as studied by corrosion casting," J. Anat., 204:123-131 (2004).
Young, V.L., et al., "Prevention of perioperative hypothermia in plastic surgery," Aesthetic Surg. J., 26:551-571 (2006).
U.S. Appl. No. 12/881,767, filed Sep. 14, 2010, issued U.S. Pat. No. 8,617,230.
U.S. Appl. No. 14/143,436, filed Dec. 30, 2013, issued U.S. Pat. No. 9,549,844.
Office Action issued in U.S. Appl. No. 12/881,767 dated Apr. 11, 2013.
Office Action issued in U.S. Appl. No. 14/143,436 dated Apr. 7, 2016.
Office Action issued in U.S. Appl. No. 14/143,436 dated Jul. 7, 2016.
Notice of Allowance issued in U.S. Appl. No. 12/881,767, dated Oct. 11, 2013.
Notice of Allowance issued in U.S. Appl. No. 14/143,436, dated Dec. 9, 2016.
U.S. Appl. No. 13/990,222, filed Aug. 5, 2013, issued U.S. Pat. No. 9,339,412.
Co-pending U.S. Appl. No. 15/134,166, filed Apr. 20, 2016, and it's filing history.
International Report on Patentability and Written Opinion, dated Mar. 20, 2012, in connection with related International Application No. PCT/US2010/048774.
International Search Report, dated May 30, 2011, in connection with related International Application No. PCT/US2010/048774.
International Search Report, dated Jun. 26, 2013, in connection with corresponding International Application No. PCT/US2011/062380.
International Search Report, dated Apr. 16, 2013, in connection with related International Application No. PCT/US2012/072030.
International Search Report, dated Apr. 16, 2013, in connection with related International Application No. PCT/US2012/072037.
European Office Action, dated Aug. 23, 2013, in connection with related European Application No. 10817719.7.
Second Office Action, dated Apr. 3, 2014, issued by the European Patent Office in connection with corresponding European Application No. 10817719.7.
Office Action issued in Canadian Application No. 2,774,346 dated Jul. 22, 2016.
Office Action issued in Canadian Application No. 2,774,346 dated Apr. 28, 2017.
Office Action received in connection with Chinese Application No. 201611145639.4, dated Apr. 28, 2020.
Chinese Office Action (and English Translation) dated Sep. 17, 2019, received in connection with Chinese Application No. 201611145639.4, 13 pages.
Chinese Office Action, dated Nov. 15, 2018, received in connection with Chinese Application No. 201611145639.4, 13 pages.
Chinese Office Action, dated Jun. 4, 2019, received in connection with Chinese Application No. 201611145639.4, 12 pages.
Office Action issued in Chinese Application No. 2010800466641 dated Dec. 17, 2013, 7 pages.
Office Action issued in Chinese Application No. 2010800466641 dated Sep. 17, 2015, 6 pages.

\* cited by examiner

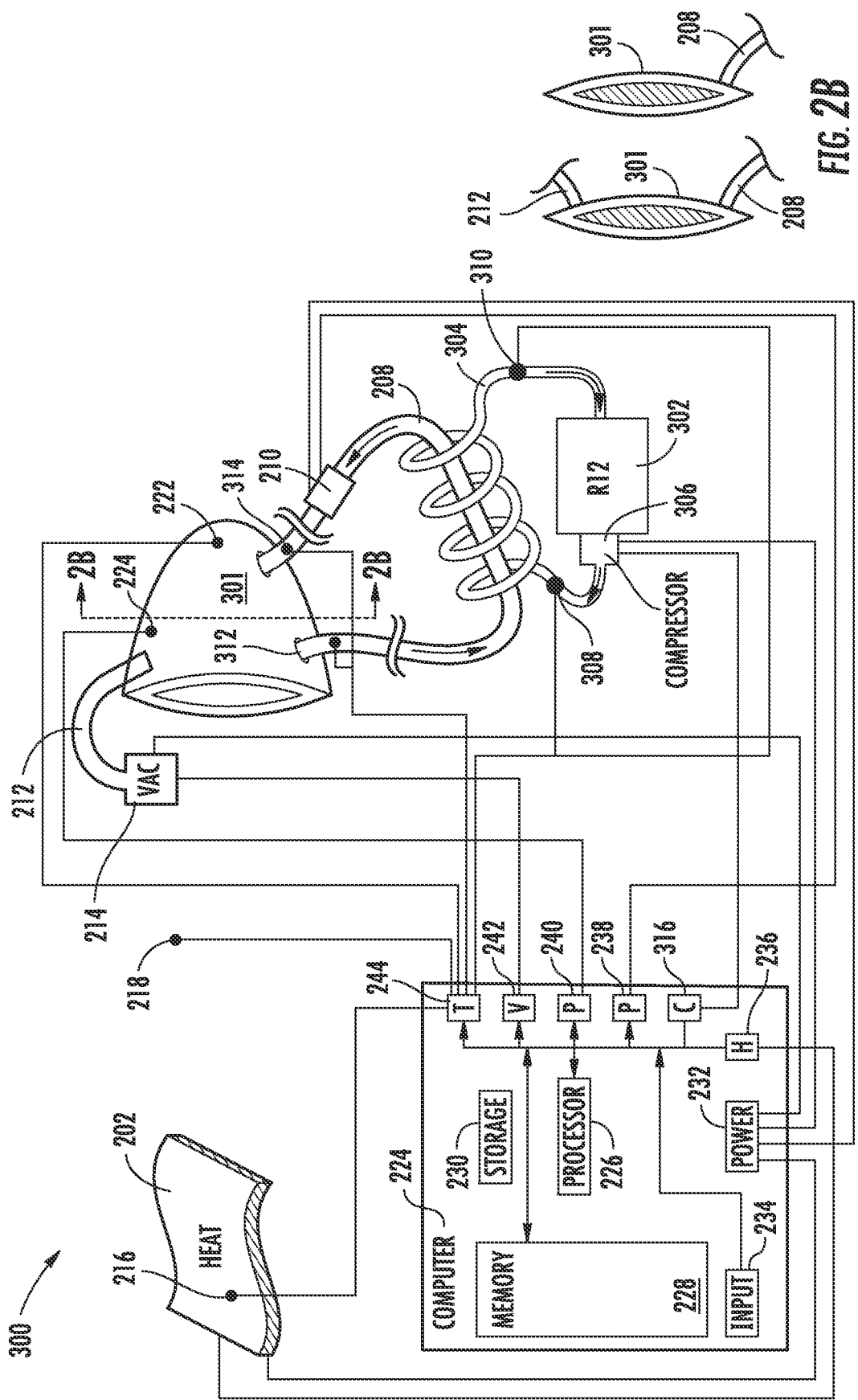

ALTERING TEMPERATURE IN A MAMMALIAN BODY

CROSS REFERENCE TO RELATED APPLICATIONS

This application is a continuation of U.S. application Ser. No. 15/377,644, filed Dec. 13, 2016, which is a continuation of U.S. application Ser. No. 14/143,436, filed Dec. 30, 2013, which is a continuation of U.S. application Ser. No. 12/881,767, filed Sep. 14, 2010, which claims the benefit of U.S. Provisional Patent Application No. 61/276,764, filed Sep. 16, 2009 and U.S. Provisional Patent Application No. 61/276,787, filed Sep. 16, 2009, all of which are incorporated herein by reference in their entireties.

TECHNICAL FIELD

The present application relates to systems and methods for altering temperature in a mammalian body. Optionally, the systems and methods can be used to lower or raise core body temperature of a mammalian subject. Optionally, the systems and methods can be used to lower or raise the temperature of glabrous skin of a mammalian subject.

BACKGROUND

The thermoregulatory system of homeotherms has an inherent ability to hold core body temperature within a small variation of a set point. Excursions, above and below the set point can cause compromised body function, injury, and even death may occur.

Operation of the thermoregulatory system is based on a complex, nonlinear network of feedback control signals and responses to adjust the thermal resistance between the body core and the environment and to modulate the rate and distribution of internal energy generation. The operation of this system is remarkably efficient over a broad spectrum of physiological states and environmental conditions.

In certain circumstances, however, the thermoregulatory system is unable to maintain the core temperature within the set operational range, or there may be therapeutic or prophylactic reasons to override the system to cause changes in the core temperature beyond the normal range. There are also situations where it may be desirable to alter the temperature of portions of the body other than the body's core. For example, it may be desirable to alter the temperature of glabrous skin in a subject.

SUMMARY

The present application relates to systems and methods for altering temperature in a mammalian body. Optionally, the systems and methods can be used to lower or raise core body temperature of a mammalian subject. Optionally, the systems and methods can be used to lower or raise the temperature of glabrous skin of a mammalian subject.

For example, provided are methods for increasing or maintaining temperature of glabrous tissue in a subject. Also provide are methods for cooling the core body temperature of a subject. Further provided are methods for warming the core body temperature of a subject.

The methods include applying heat to peripheral thermoregulatory control tissue of the subject. The applied heat increases or maintains perfusion of blood in the glabrous tissue. By increasing or maintaining perfusion, the temperature of the glabrous tissue can be optionally increased. In some aspects, cooling stimulus can be applied to the glabrous tissue with the increased or maintained perfusion. In other aspects, a warming stimulus can be applied the glabrous tissue with the increased or maintained perfusion. When a cooling stimulus is used, the core temperature of the subject can be reduced. When a warming stimulus is used, the core temperate of the subject can be increased.

Optionally, the peripheral thermoregulatory control tissue is located in the cervical spinal region or in the lumbar spinal region of the subject. Negative pressure can also be applied to the glabrous tissue. The negative pressure can be used to increase or maintain perfusion of blood in the glabrous tissue.

For the core cooling methods, the subject may have suffered cardiopulmonary arrest, ischemic stroke, subarachnoid hemorrhage, hepatic encephalopathy, trauma, brain surgery, perinatal asphyxia, infantile encephalitis, a hyperthermic-inducing event, or acute brain injury. With these conditions, the methods can be used to cool the core body temperature and to establish hypothermia in the subject. For the warming methods, the subject may have suffered a hypothermia-inducing event.

Also provided are systems for cooling the core body temperature of a subject. The systems include a heating device configured to apply heat to peripheral thermoregulatory control tissue of the subject. The applied heat increases or maintains perfusion of blood in the glabrous tissue. The systems further comprise a cooling device configured to apply a cooling stimulus to the glabrous tissue and may optionally comprise a device adapted to apply negative pressure to the glabrous tissue.

The heating device can be adapted to deliver heat to the cervical spinal region and/or lumbar spinal region of the subject. Optionally, the heating device is configured to heat the skin overlying the peripheral thermoregulatory control tissue of the subject. Optionally, the heating device is configured to heat the tissue below the skin overlying the peripheral thermoregulatory control tissue of the subject. The heating device can be optionally selected from the group consisting of a resistive heating device, an electromagnetic based heating device, a light based heating device, an ultrasound based heating device, and an exothermic chemical reaction based heating device. The cooling device can be adapted to provide a cooling stimulus to a palmar and/or to a plantar region and/or to an area of glabrous skin on the face of the subject. Optionally, the cooling device comprises a liquid that is cooled to a temperature lower than the glabrous tissue.

Also provided are systems for warming the core body temperature of a subject. The systems include a heating device configured to apply heat to peripheral thermoregulatory control tissue of the subject. The applied heat increases or maintains perfusion of blood in the glabrous tissue. The systems further comprise a warming device configured to apply a warming stimulus to the glabrous tissue and may optionally comprise a device adapted to apply negative pressure to the glabrous tissue.

The heating device can be adapted to deliver heat to the cervical spinal region and/or the lumbar spinal region of the subject. Optionally, the heating device is configured to heat the skin overlying the peripheral thermoregulatory control tissue of the subject. Optionally, the heating device is configured to heat the tissue below the skin overlying the peripheral thermoregulatory control tissue of the subject. The heating device can be optionally selected from the group consisting of a resistive heating device, an electromagnetic based heating device, a light based heating device, an ultrasound based heating device, and an exothermic chemical reaction based heating device. The warming device can be adapted to provide a warming stimulus to a palmar and/or to a plantar region and/or to an area of glabrous skin on the face of the subject. Optionally, the warming device can be selected from the group consisting of a resistive heating device, an electromagnetic based heating device, a light based heating device, an ultrasound based heating device, and an exothermic chemical reaction based heating device.

These and other features and advantages of the present invention will become more readily apparent to those skilled in the art upon consideration of the following detailed description and accompanying drawings, which describe both the preferred and alternative embodiments of the present invention.

BRIEF DESCRIPTION OF THE DRAWINGS

FIG. 2A is a schematic illustration of an example system for altering temperature in a mammalian body.

FIG. 2B is a schematic cross sectional illustration of the cooling device 301 of FIG. 2A taken across the line 2B-2B.

Like reference numbers and designations in the various drawings indicate like elements.

DETAILED DESCRIPTION

Figure 1:
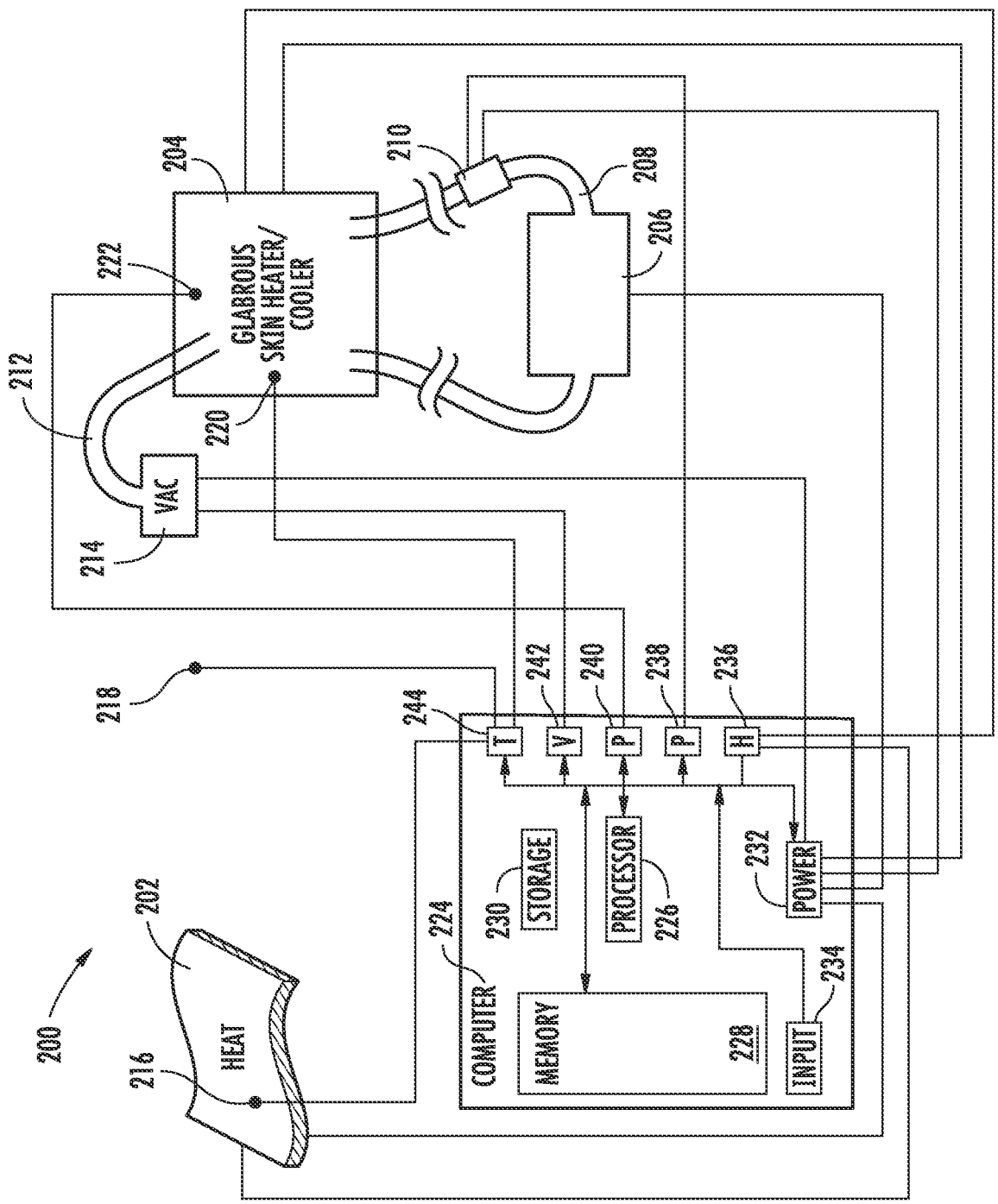
FIG. 1 is a schematic illustration of an example system for altering temperature in a mammalian body.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

Mammalian body temperature is tightly regulated by an internal autonomic regulatory system which comprises central controllers and the blood circulatory system, plus mechanisms for adjusting the rate and locations of internal energy generation. The circulatory system covers the entire body and delivers heat from the body core to the peripheral areas, or, in less frequent circumstances, delivers heat from the periphery to the core.

Alteration of the blood flow through the skin plays an important role in temperature regulation. For example, in nonglabrous skin vasodilation (dilation of arterioles and small arteries) and vasoconstriction (constriction of arterioles and small arteries) increase or decrease blood flow to match thermoregulatory needs. Both the processes of vasoconstriction and vasodilation are regulated by active means in response to a combination of local, systemic, and central inputs.

Normally, when body and/or environmental temperatures are high, vasodilation favors high blood flow to the surface areas involved with heat exchange, thus increasing heat loss to the environment and reduction in the deep body core region temperature. As environmental and/or body temperatures fall, vasoconstriction reduces blood flow to the skin surfaces and minimizes heat loss to the environment.

One important effector of the thermoregulatory system is controlled by blood flow to specialized skin areas of the body at non-hairy skin surfaces, also referred to as glabrous skin, and includes skin at the palms of the hands, soles of the feet, and the ears, cheeks, forehead, and nose regions or any area of skin that contains a special vascular structure that is effective in affecting heat transfer between circulating blood and the body surface. Basal to the skin in these areas are unique anatomical vascular structures called venous plexuses. These structures serve to deliver large volumes of blood adjacent to the skin surface under conditions of vasodilation. By this delivery of blood, significant heat transfer may occur for the maintenance of internal organs within a functional temperature range.

Blood is permitted to pass through the venous plexus structures by way of arteriovenous anastomoses (AVAs) that are blood vessels that directly shunt arterial blood to the veins without passing through the capillaries. When vasodilated, the AVAs have a diameter an order of magnitude or greater than the capillaries, thereby providing a low flow resistance pathway for blood circulating from the heart. At full vasodilation the AVAs present among the lowest flow resistance of the entire circulatory system, resulting in a considerable fraction of the total cardiac output flowing through them. The relative proximity of the cutaneous AVAs to the surface of the body, and the potential for carrying large rates of blood flow make the AVAs a very effective heat exchange vehicle in the thermoregulatory apparatus. The AVAs are an integral part of the body's heat transfer system, providing important thermoregulatory control. Regulation of the AVA flow diameter is unique in comparison to the cutaneous microcirculation in nonglabrous skin. Adjustment in the flow resistance through AVAs is controlled by activation and relaxation of vasoconstriction.

Thermal stimulation of the peripheral thermoregulatory control tissue can cause an increase in the mean value of AVA flow wherein the vasomotive fluctuations are superimposed at a higher average flow. Removal of the thermal stimulation of the peripheral thermoregulatory control tissue can result in a lowering of the mean AVA flow as the relaxing input to the AVA vasoconstriction activity is diminished. This direct coupling between thermal stimulation of peripheral thermoregulatory control tissue and AVA perfusion rate offers a powerful opportunity to manipulate convective heat transfer processes involving glabrous skin, including convective movement of energy between the body surface and core via the circulation of blood to and from the AVAs, without involving inputs from the thermoregulatory control tissue of the hypothalamus.

The operation of this system is remarkably efficient over a broad spectrum of physiological states and environmental conditions. In certain circumstances, however, the thermoregulatory system is unable to maintain the core temperature within the set operational range, or there may be therapeutic or prophylactic reasons to override the system to cause changes in the core temperature beyond the normal range. In these cases, devices and methods are applied interventionally either to assist or to override the thermoregulatory system.

A different challenge in regulating the body core temperature arises under conditions for which the brain becomes starved of oxygen owing to a medical event such as cardiac arrest, stroke, or traumatic brain injury. Laboratory and clinical data indicate that if the body core, and particularly the brain, temperature can be reduced by as little as 2° C. within approximately 90 minutes of the precipitating event, a significant therapeutic benefit is realized to limit mortality and morbidity. Unfortunately, the function of the thermoregulatory system resists lowering the core temperature from a state of normothermia via cutaneous vasoconstriction to increase the thermal resistance between the skin and core and by shivering to increase the rate of internal metabolic heat generation.

An example is the use of therapeutic hypothermia to treat a subject who is suffering an episode of brain ischemia that may be caused by stroke, cardiac arrest, traumatic brain injury, or another condition. Such a subject may be in an initial state of AVA vasoconstriction. At this time, when therapeutic hypothermia is applied within a short time window of efficacy, according to the methods of the disclosure, a state of AVA vasodilatation is induced on demand. For example, using the described methods, systems and devices therapeutic hypothermia can be induced in a subject at about 90 minutes or less following an insult to a subject that would benefit from therapeutic hypothermia. For example, following an insult to the brain, heart or other tissue, therapeutic hypothermia can be induced at about 90 minutes or less from the insult.

Surface cooling over large areas of skin is ineffective because it induces vasoconstriction, thereby eliminating direct circulation of blood between the skin and core, which is a much more effective heat transfer mechanism than parasitic conduction through the body structures. Alternatively, methods have been developed for cooling the core directly by infusion of large volumes of chilled saline solution into the circulatory system. Collateral drawbacks associated with this technology include the necessity of cannulating the circulatory system under sterile conditions and introduction of added volume of fluid into the blood which can result in elevated blood pressure. Since this technology is typically practiced in a medical facility, precious time during the window of therapeutic opportunity (approximately 90 minutes) is lost during transport following the precipitating event to a medical facility and the initiation of therapy. The systems and methods described herein can be used to produce a state of therapeutic hypothermia on demand following a brain ischemia producing event within 90 minutes.

Another thermoregulatory challenge occurs when a person is hypothermic with a necessity of being rewarmed to normotheria in the absence of conditions such as anesthesia that would result in a state of vasodilation in the cutaneous circulation. The most effective heat transport mechanism to warm the body core is by the circulation of blood between the skin and the core. However, hypothermia-induced cutaneous vasoconstriction blocks this mechanism. The systems and methods described herein bypass this state to gain convective access to the body thermal core for warming.

A further need arises when a person is subjected to a cold environment for a period of time sufficient to elicit vasoconstriction of the AVAs, particularly in the hands and feet. Although this standard thermoregulatory response is conservative of the body's core energy and is important for long term survival, in the short term it creates a condition of discomfort, with a strong sensation of having cold hands and feet. Typical responses are: to adopt behaviors to attempt to warm the hands and feet; to provide increased insulation surrounding the hands and feet; and/or to apply various devices to actively warm the hands and feet. However, these measures are not generally effective in the short term since they do not address the source of cold sensation, that being vasoconstriction of AVAs.

The described methods and devices can be used to trigger the opening of vasoconstricted AVAs on demand, in the absence of extreme local conditions that may override all other control signals, to produce a high level of blood perfusion through glabrous skin. Vasodilation of the vasoconstricted, or more mechanistically, relaxation of the vasoconstriction of AVAs, enables the resolution of all of the foregoing thermal physiological challenges.

Referring to FIG. 1 an example system 200 is illustrated. The system 200 can be used to heat or cool a mammal's core temperature. The system can also be used to heat or cool glabrous tissue of a mammal.

The system 200 includes a heating element 202, also referred to as a heating device. The heating element 202 can comprise any device that can be used to heat skin and/or underlying tissues of a mammalian body. For example, the heating element may comprise a resistive heating element and thus act as a traditional heating pad when supplied with electrical current. In this regard, the heating element 202 can receive current from a power source 232. The heating element 202, however, is not limited to a resistive heating device, such as a heating pad.

The heating element 202 can be any device that can raise the temperature of a mammal's skin and/or the tissues underlying the skin of a mammal's body. One skilled in the art will therefore appreciate that many alternative heating elements can be used. Several other non-limiting examples include exothermic chemical reactions, application of electromagnetic energy, light, ultrasound or other energy to the skin/underlying tissues. Thus, many different devices and process may be applied for heating the peripheral thermoregulatory control tissue to raise its temperature to a degree wherein the level of stimulation reaches the threshold requisite to cause relaxation of the vasoconstrictive effect on AVAs in glabrous skin. Example heating devices use surface delivery of heat to the skin. Other example heating devices use deep tissue delivery of heat.

The increase in temperature caused by the heating element can be measured and/or monitored by a temperature sensing device 216. The temperature sensing device 216 can be positioned in proximity to the heating element 202 such that it can optionally determine temperature information including, for example, if the temperature of the skin or underlying tissues has been increased, the extent of such increase, and any temporal fluctuations in temperature in the skin or tissues proximate the heating element. Optionally, temperature information can be communicated to a temperature sensing module 244 of a computer 224. The temperature information can be processed, for example, using the processor 226 and such processed information can be used to regulate the intensity of heat and duration of heat produced by the heating element. For example, the power module 232 can also be in operative communication with the processor 226 and the temperature information can be used to increase or decrease the power supply to the heating element 202.

Heat from the heating element 202 can be used to trigger, on demand, the relaxing of vasoconstriction of AVAs in glabrous skin. There are numerous benefits of increased AVA perfusion such as gaining access to cutaneous blood flow for convective heat transfer of blood with heating and cooling sources placed on the surface of the skin to provide efficient transport of energy between the body core and the body exterior surface via the circulation of blood. Another benefit of increased AVA perfusion from a state of vasoconstriction is the added heat transfer to the skin from warm blood circulating from the body core, thereby reducing or eliminating a feeling of coldness experienced in vasoconstricted glabrous skin of the hands and feet, which may be perceived as being uncomfortable.

A method for causing AVAs to vasodilate is to apply a heating source to tissues at a site of thermoregulatory control that is peripheral to the preoptic hypothalamus. Thus, thermal stimulation of peripheral thermoregulatory control tissue via heating by multiple alternative means include, but are not limited to, (a) a heat source applied to the surface of the skin, (b) deep heating via an infrared source, (c) deep heating via an electromagnetic source such as in diathermy, and (d) deep heating via an ultrasound source. Peripheral thermoregulatory tissue includes tissue that when heated exerts control on AVAs and does not include the brain and hypothalamus.

Figure 3A:
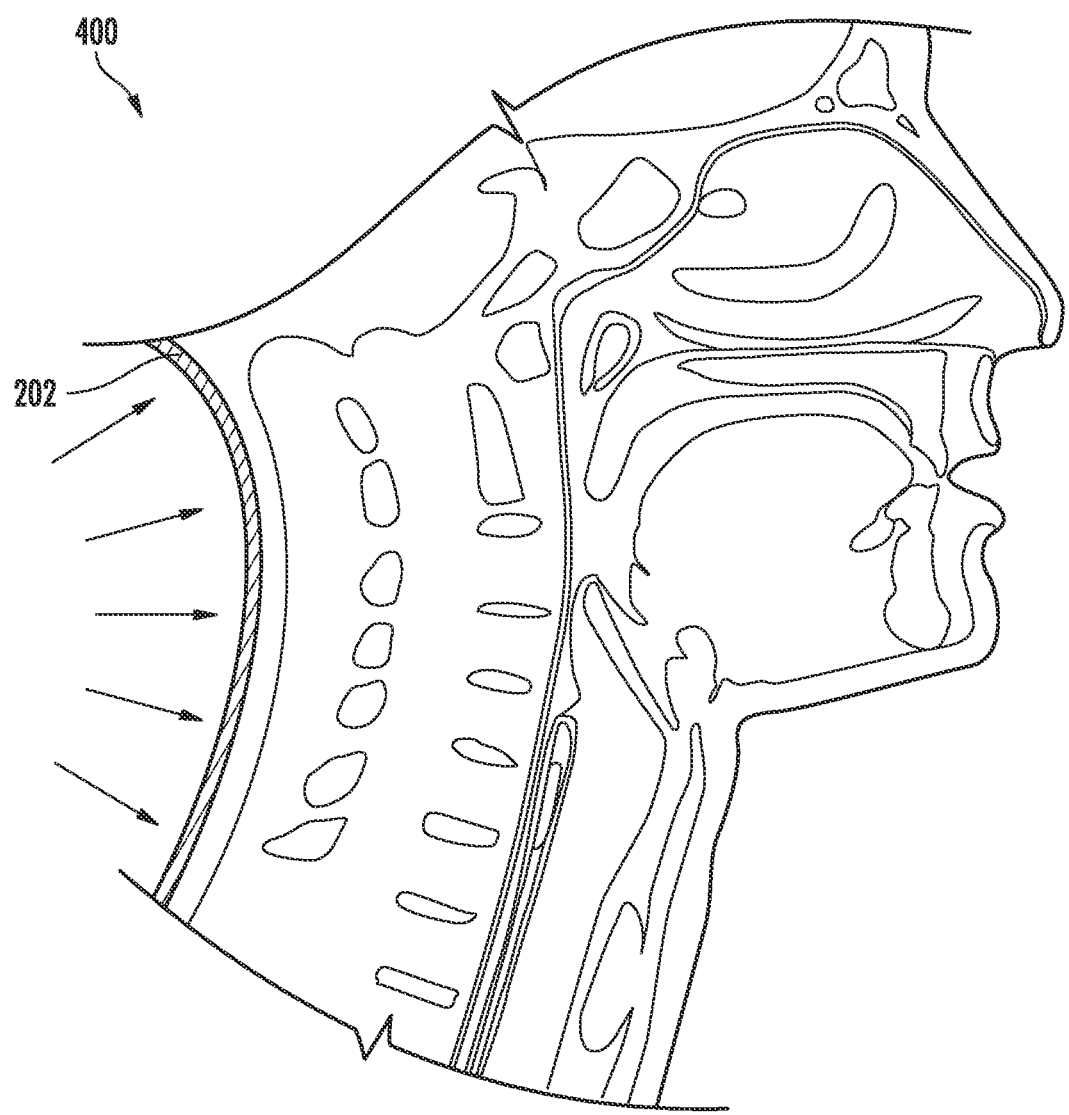
FIG. 3A is a schematic illustration of heat application to the cervical spinal thermoregulatory tissue of a subject.
Figure 3B:
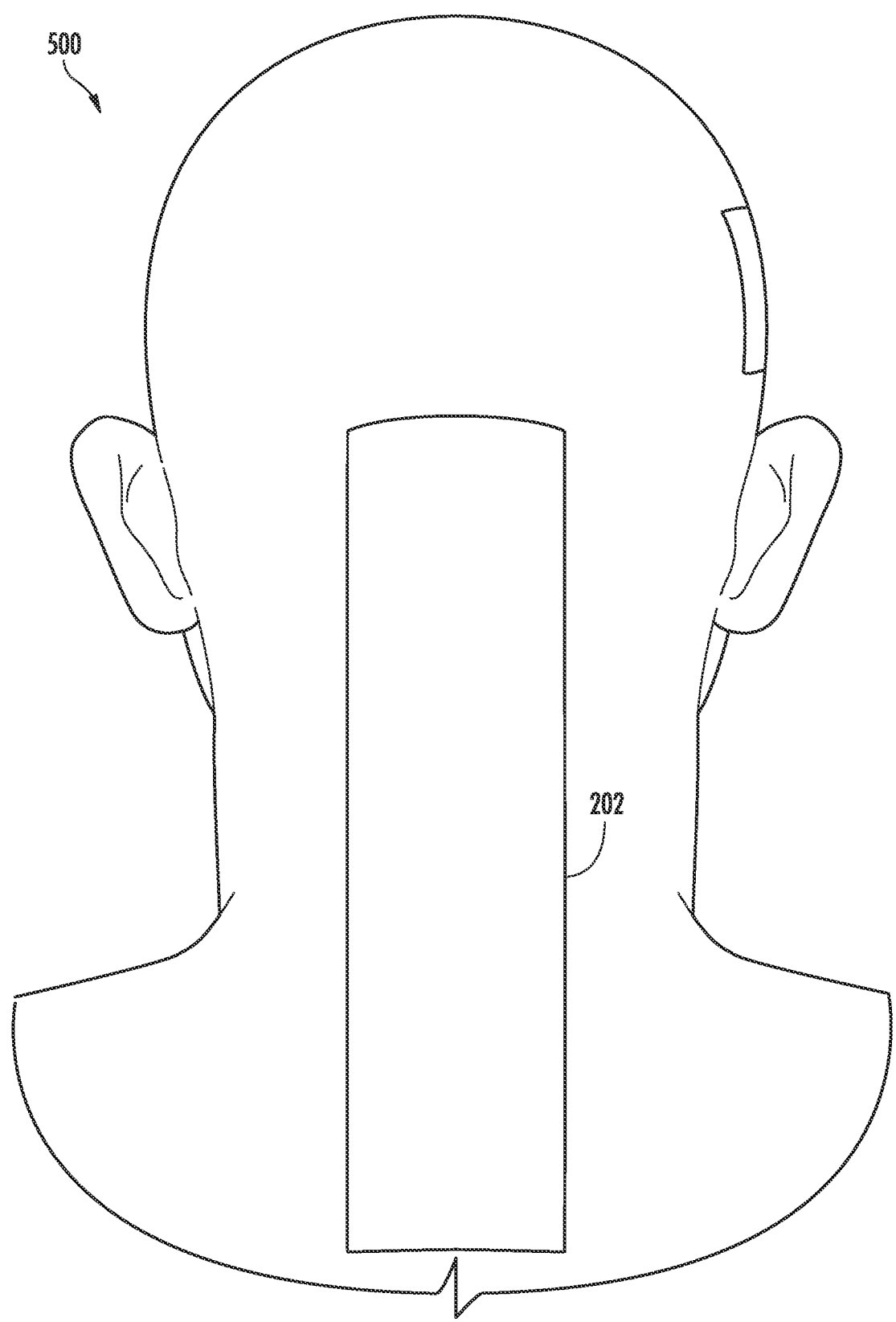
FIG. 3B is a schematic illustration of a device for heat application to the cervical spinal thermoregulatory tissue of a subject.

FIGS. 3A and 3B show that among peripheral areas that can be heated for this purpose is that tissue of and proximal to the spinal cord, including the cervical and lumbar areas that are rich in parasympathetic innervation. FIG. 3A illustrates a cross sectional view of the spine and overlying tissues during heating to stimulate blood flow through the arteriovenous anastomoses by which a heating source 202 is applied either to the skin surface or by a penetrating mechanism to reach deeper tissues through the skin and toward the spine to produce an elevated temperature in these tissues. Heat penetration is illustrated by the wave emanating from a source such as a heating pad through the cross section of the cervical spine and associated tissues.

When the peripheral area heated is the cervical spinal area the heating element or heating source 202 can be incorporated into a wearable device to that can operatively apply heat to the cervical spinal area. For example, the heating source 202 can be incorporated into a wearable pillow. Optionally, the heating source, and portions of the pillow, can be contoured to portions of the cervical anatomy of the subject to provide good thermal contact between the heating source and the skin of the subject. The pillow also optionally provides overlying thermal insulation at the site of heating.

Therefore, an effective strategy to control AVAs is to apply localized heating to the skin in an area peripheral to both the brain and to the glabrous skin containing AVAs having parasympathetic thermal innervation that controls AVA vasoconstriction. The heated area can be small so as to limit the total heat transfer to the body, avoiding causing a significant increase in the total energy of the body and a concomitant rise in core temperature. Areas other than the cervical and lumbar spine can also be heated resulting in vasodilation of AVAs. Increased blood flow through the AVAs can be readily measured using, for example, Doppler ultrasound techniques. Thus, areas peripheral to the preoptic hypothalamus that when heated cause increased blood flow through the AVAs can be readily determined.

A period of thermal stimulation on the skin surface is used to allow sufficient time for heat to diffuse inwardly to reach a depth at which the thermal receptors are located interior or proximal to the spine. The stimulation signal to cause AVA vasodilation may also depend on the magnitude of the spatial temperature gradient from the surface of the skin inward and/or on the temporal gradient causing a rise in temperature. A stimulating signal may be a combination of the temperature and temperature gradient at the stimulation site.

The heating process is conducted in a manner wherein the temperature of the target tissue is increased sufficiently to cause the relaxation of vasoconstricted AVAs. The amount and method of heating can be sufficient to cause a rise in the target tissue to at least 39° C. In other embodiments, to at least 40° C. In other embodiments, to at least 41° C. In other embodiments, to at least 42° C. In other embodiments, to at least 43° C. In all embodiments, the temperature of the target tissue does not exceed a safety threshold above which thermally induced injury occurs. For most tissues, this threshold temperature is 43° C.

Therefore, the level of thermal stimulation can be above a threshold for causing AVA vasodilation and below a threshold for causing thermal injury. The level of stimulation may be within the range of temperatures of 39° C. to 43° C. for 1 minute or more to cause vasodilation, depending on the initial thermal state of the body. For example, the level of stimulation may be within the range of temperatures of 39° C. to 43° C. for 5 minutes or more to cause vasodilation, depending on the initial thermal state of the body and the method and intensity of heating.

For methods that involve heating the skin surface, a minimal period of thermal stimulation may be required to allow sufficient time for heat to diffuse inwardly to reach a depth at which the thermal receptors are located that provide inputs that control blood flow to the AVAs. The stimulation signal to cause AVA vasodilation may also be dependent on the magnitude of the temperature gradient from the surface of the skin inward and the time rate of change of temperature.

The heating process has a duration sufficient to cause an initial increase in vasodilation of AVAs to allow greater blood flow. Optionally, the heating process is maintained until the AVA vasodilation reaches a maximum value, which can be measured, for example, by Doppler velocimetry.

Optionally, the heating process will be maintained for the entire period for which increased blood flow through the AVAs is desired. The heating process can be activated in a time-wise oscillatory manner in which the magnitude of heating is alternatively increased and decreased. The periodicity of the increasing and decreasing heating may have a cycle varying from less than one second to more than ten minutes. Optionally, where periodicity of heating is applied, the period of a single cycle can be more than one second and less than 10 minutes.

For embodiments wherein a regime of alternatively increasing and decreasing heating is applied, the relative periods of greater and lesser or no heating may be equal or unequal. Either the period of greater heating or the period of lesser or no heating may be larger if they are not equal. For all embodiments, the magnitude of heating can be increased and decreased at least once, and in some embodiments, more than one time. For all embodiments the rate of increase of heating and the rate of decrease of heating may or may not be equal, and both may or may not be linear. For embodiments for which the heating is not constant for its duration, the rates and time-wise patterns of increasing and decreasing magnitudes of heating may be designed and adjusted to maximize the simulation of the target tissue in the peripheral thermoregulatory control center tissue that regulates the relaxing of vasoconstricted AVAs. Any desired heating protocol can be implemented using the computer 224. The heating protocols can be programmed and/or modified by input 234 from a user.

The described systems and methods can cause the AVAs to become vasodilated in their base state so that the flow of blood through glabrous skin can serve as a convective heat transfer medium. If the AVAs are vasoconstricted in a mode that has the objective of conserving the energy of the body core, a signal consistent with the body rejecting energy from the core can be used to cause the AVAs to vasodilate. A primary vaso-control signal to the AVAs originates in the hypothalamus and is based on the temperature of that tissue. For applications with the objective of cooling the brain for medical purposes, such as in therapeutic hypothermia, warming the hypothalamus to cause AVA vasodilation is counter-productive.

Figure 5:
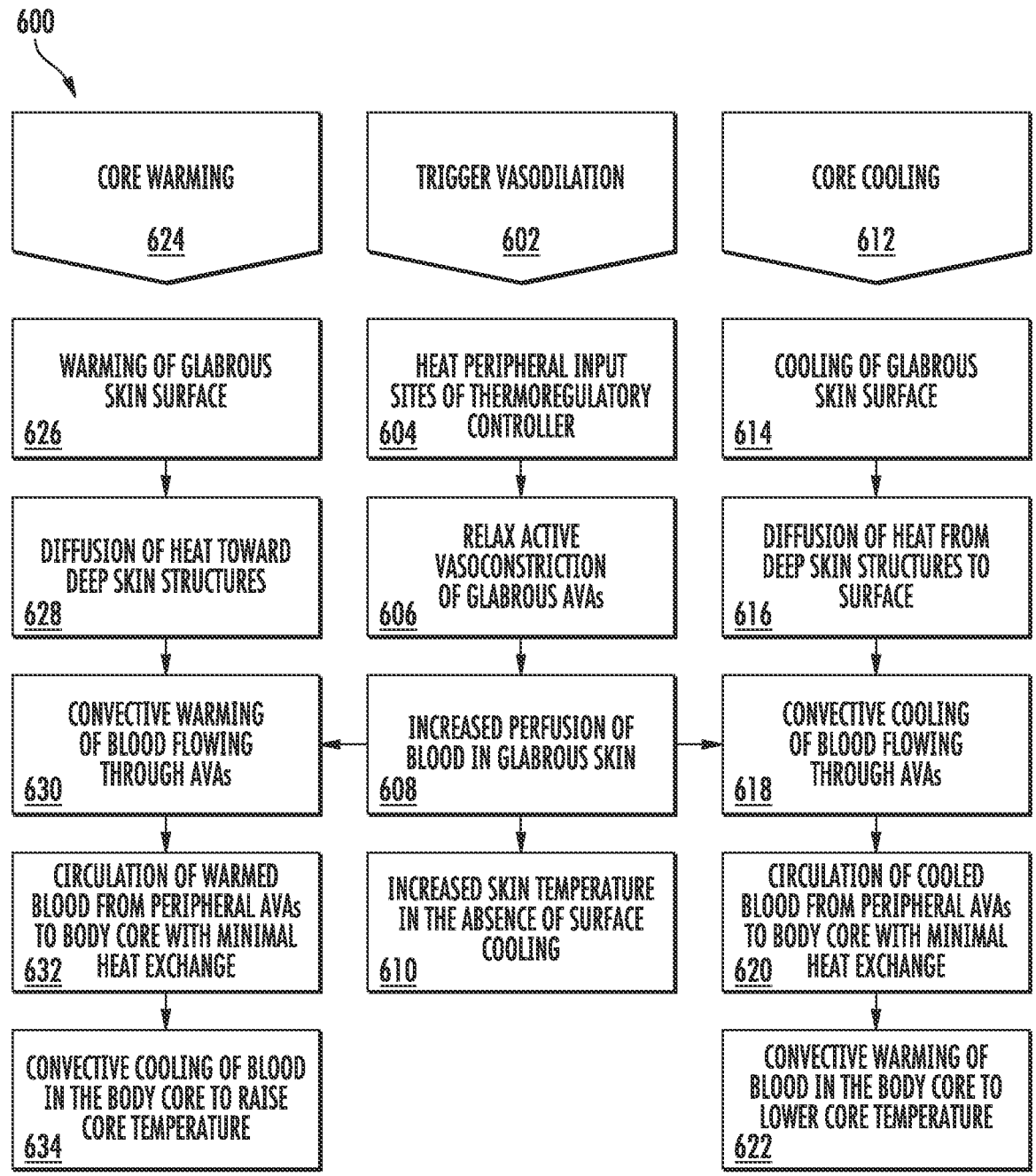
FIG. 5 is a flow diagram showing example methods for altering temperature in a mammalian subject.

Referring now to FIG. 5, the combined physiological and thermodynamic mechanism of action is illustrated. For example, as shown in 602, vasodilation can be triggered by heating peripheral input sties of thermoregulatory control 604. The heating can relax the active vasoconstriction of glabrous AVAs 606. The relaxing of vasoconstriction 606 leads to increased perfusion of blood in glabrous skin 608. The increased perfusion of blood leads to increased skin temperature in the absence of surface cooling 610. Thus, the system 200 shown in FIG. 1 can optionally be used to increase glabrous skin temperature. In this example, additional heating or cooling of the glabrous skin is optional.

A method is therefore provided for heating the glabrous skin of a mammalian subject comprising applying heat to an area of the subject that causes vasodilation of AVAs located in the glabrous tissue. This method may be desirable when increasing the temperature of glabrous skin is desirable, such as, for example, when the subject's hands, feet or face is cold. To implement this method, a system can be used that comprises a heating element applied to an area of the subject that causes vasodilation of AVAs located in the glabrous tissue. For example, such a system can include a heating element configured for heating the skin or tissues of the cervical spinal or lumbar spinal region.

In other examples, the described systems can be used to heat or cool a subject's core temperature. Referring again to FIG. 1, the system 200 can comprise a glabrous skin cooler or heater device 204. For cooling operation, the device 204 can receive chilled or cooled fluid or gas trough a conduit 208. A pump 210 can actively pump the cooled fluid or gas into and through the device 204. The movement of cooled fluid or gas through the device cools the device. A refrigeration device 206, such as a thermoelectric refrigerator, can be used to cool the fluid or gas that is circulated through the device 204 and conduit 208. The pump 210 and refrigeration device can both be in operative communication with the computer 224 such that the temperature of the device and cooling protocol of the device can be controlled by the computer and through user input 234. If heating of the glabrous skin is desired the device 204 can provide heating as an alternative to cooling. The device can apply heat to the glabrous skin and underlying tissues using any of the mechanisms described above in relation the heating element 202.

In addition, the system can comprise a temperature sensor 220 positioned to detect the temperature of the device 204 or to detect the temperature of the glabrous skin in proximity to the device 204. This temperature information can be communicated to the computer 224 where it can be processed to determine desired cooling or heating characteristics of the device 204 on the glabrous skin.

Optionally, the system 200 further comprises a vacuum 214. The vacuum 214 is in operative communication with the device 204 by way of the vacuum line 212. The vacuum can be used to exert negative pressure on the glabrous skin on which the device 204 is cooling or heating. The negative pressure can be used to enhance the dilatation of AVAs in the subject's glabrous skin. As shown in the system 200, the vacuum and therefore the negative pressure exerted on the glabrous skin can be controlled by the computer 224. Specifically, the vacuum is in operative communication with the computer 224 by way of a vacuum module 242. In addition, the device 204 can be equipped with a pressure sensor 222 that is in operative communication with the computer 224 by way of a pressure sensing module 240. In this way, the computer 224 may process pressure information and temperature information and this information may be used to adjust factors affecting the operation of the device 204 such as the temperature or temporal characteristics of the cooling fluid or gas circulated through the device 204 or the negative pressure or temporal characteristics thereof.

The system 200, when used with the cooling or heating device 204 can be used to alter the core temperature of a subject's body. In this regard, a temperature sensor 218 can by optionally positioned to take or to monitor the central temperature of the subject. The temperature sensor 218 can be positioned in suitable way for obtaining one or more central temperature reading from a subject. For example, the temperature sensor can be optionally placed in the subject's ear canal, oral cavity or rectum. The temperature sensor can also be optionally paced on the forehead or axillary region of a subject.

Without limiting any specific embodiment to any particular mechanism of action, vasodilating and/or enlarging AVAs by heating using the heating element 202 causes diversion of a large fraction of cardiac output to the skin. The skin mediates heat exchange between blood flowing through the AVAs and the environment, which heat may then be convected via the circulation of blood to (for heating) or from (for cooling) the body thermal core.

The enhanced flow of blood through vasodilated AVAs therefore provides an opportunity to cause an increased flow of energy between the body surface and body core by applying heating or cooling to the glabrous skin surface, thereby heating or cooling blood perfused through the AVAs that will then circulate back to the core at a temperature that will induce heating or cooling of the core tissues.

Referring again to FIG. 5, a subject's core temperature can optionally be cooled 612. The steps of cooling the subject's core temperature include cooling the glabrous skin 614. Such cooling can be accomplished as described above using the device 204. Cooling of the glabrous skin 614 causes diffusion of heat from deep skin structures to the surface 616. In addition, the method can comprise increasing the perfusion of blood in the glabrous skin as shown in steps 602-608.

The combination of the increased perfusion of blood in the glabrous skin 608 and diffusion of heat from deep skin structures to the surface 616 results in convective cooling of blood flowing through AVAs in the glabrous skin 618. The cooled blood is circulated from the peripheral AVAs to the body core with minimal heat exchange 620. This results in convective warming of the blood in the body core to lower the core temperature 622. A peripheral thermal stimulation may be required to be maintained past the initial time at which vasodilation starts, up to the entire period during which cooling may be applied to glabrous skin with vasodilated AVAs to produce a progressively increasing state of therapeutic hypothermia. Optionally, surface cooling is provided to an area of glabrous skin and simultaneous warming to a small area of skin rich in thermal parasympathetic innervations that controls AVA blood flow.

In the described systems and methods, cooling may be produced by the application of one or more pre-chilled gel packs having a mass and initial temperature sized to produce a desired drop in body thermal core temperature, or, alternatively, warming may be produced by application of one or more pre-warmed gel packs to produce a required increase in body thermal core temperature. The pre-chilled and pre-warmed gel packs may be reusable or disposable following use.

Cooling may optionally be produced by the mixing of chemical elements contained within a flexible package that undergo an endothermic process when mixed thereby reducing the temperature of the mixture. The mixture components may be prepackaged in a single pack with interior barriers that separate the chemical components until the time when the cooling is to be produced, whereupon the barriers may be ruptured to enable the mixing of components with an endothermic effect.

Also referring to FIG. 5, a subject's core temperature can optionally be heated 624. The steps of heating the subject's core temperature include heating the glabrous skin 626. Such heating can be accomplished as described above using the device 204. Heating of the glabrous skin 626 causes diffusion of heat away from the skin surface and towards the deep skin structures 628. In addition, the method can comprise increasing the perfusion of blood in the glabrous skin as shown in steps 602-608. The combination of the increased perfusion of blood in the glabrous skin 608 and diffusion of heat towards the deep skin structures results in convective warming of blood flowing through AVAs in the glabrous skin 630. The warmed blood is circulated from the peripheral AVAs to the body core with minimal heat exchange 632. This results in convective cooling of the blood in the body core to raise the core temperature 634. Optionally, surface warming is provided to an area of glabrous skin and simultaneous warming to a small area of skin rich in thermal parasympathetic innervations that controls AVA blood flow.

Warming may be produced by mixing chemical elements that undergo an exothermic process causing the temperature of the mixture to rise. In some embodiments, warming may be generated by exposing a sealed package of chemicals to oxygen or air by rupturing an impermeable sealing cover resulting in a sustained increase in temperature of the pack. The chemical mixing packs that operate by rupturing a membrane or barrier or cover are disposable after a single use.

Pre-chilled and pre-warmed gel packs and endothermic and exothermic chemical mixing packs may all be flexible allowing for conformation of the pack to the shape of the glabrous skin surface, thereby ensuring better thermal contact than if the cooling or warming substrate is rigid.

In some embodiments the chilled or warmed packs may be located peripherally to the glabrous skin where they cool or warm a liquid that is circulated under the action of a pump to a flexible bladder positioned in contact with glabrous skin.

In some embodiments, a warming or cooling pack applied to glabrous skin may be equipped with one or more attachment straps to aid in maintaining effective thermal contact between the pack and glabrous skin. These embodiments may be particularly useful under conditions in which a subject is unable to actively participate in ensuring that a best level of heat transfer occurs between the pack and skin, such as when the subject is not aware of the treatment process or is unconscious.

Referring now to FIGS. 2A and 2B, an example system 300 is shown for cooling core body temperature. As described with relation to FIG. 1, the example system comprises a computer 224 and a heating element 202. The heating element can be used to heat subject tissue to lead to dilation of AVAs in the subject's glabrous skin. A temperature sensor 216, also described, above can detect the temperature of the skin and/or tissue in proximity to the heating element 202. As the temperature sensor 216 is in operative communication with the computer 224 temperature readings from the temperature sensor can be used to provide a desired level of heating from the heating element 202.

The system 300 further comprises a heat exchanger in communication with the conduit 208 comprising the cooling fluid or gas. The heat exchanger can comprise a compressor 306 and a source of refrigerant 302, such as R12. The heat exchanger can further comprise a temperature sensor 308 to sense the temperature of refrigerant prior to the conduit 208 and a second temperature sensor 310 subsequent to the conduit. Refrigerant can be circulated through the tube 304 to cool fluid in the conduit 208.

The conduit 208 can hold cooled fluid or gas that can be pumped into and through a cooling sleeve 301. The cooling sleeve 301 can be optionally placed over the glabrous skin of the hand, foot, or face. FIG. 2B shows a cross section of the sleeve across the line 2B-2B. Two additional temperature sensors can be positioned to monitor the temperature of the fluid or gas in the conduit. A first temperature sensor 314 can detect/monitor the temperature of fluid or gas entering the sleeve. A second temperature sensor 312 can detect/monitor the temperature of fluid or gas leaving the sleeve.

Each temperature sensor 308, 310, 312 and 314 may be in operative communication with the computer 224 through a temperature sensor module 244. In addition, the compressor 306 and the pump 308 are also in operative communication with the computer 224 through a compressor 316 and pump 240 module respectively. Information collected from the temperature sensors and the flux through the heat exchanger can be used to cool the fluid or gas in the conduit 208, and thus the sleeve 301 to a desired temperature.

As shown in the systems 200 and 300, the methods described herein can be implemented via a general-purpose computing device in the form of a computer 224. The components of the computer 224 can include, but are not limited to, one or more processors or processing units 226, a system memory 228, and a system bus that couples various system components including the processor 226 to the system memory 228.

The system bus may represent one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. The bus, and all buses specified in this description, can also be implemented over a wired or wireless network connection and each of the subsystems, including the processor 226, a mass storage device 230, an operating system, application software, data, a network adapter, system memory, an Input/Output Interface, a display adapter, a display device, and a human machine interface, can be contained within one or more remote computing devices at physically separate locations, connected through buses of this form, in effect implementing a fully distributed system.

The computer 224 typically includes a variety of computer readable media. Such media can be any available media that is accessible by the computer 224 and includes both volatile and non-volatile media, removable and non-removable media. The system memory 228 includes computer readable media in the form of volatile memory, such as random access memory (RAM), and/or non-volatile memory, such as read only memory (ROM). The system memory 228 typically contains data such as data and and/or program modules such as operating system and application software that are immediately accessible to and/or are presently operated on by the processing unit 226. The computer 226 may also include other removable/non-removable, volatile/non-volatile computer storage media. A mass storage device 230 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device 230, including by way of example, an operating system and application software. Each of the operating system and application software (or some combination thereof) may include elements of the programming and the application software. Data can also be stored on the mass storage device. Data can be stored in any of one or more databases known in the art. Examples of such databases include, DB2®, Microsoft® Access, Microsoft® SQL Server, Oracle®, mySQL, PostgreSQL, and the like. The databases can be centralized or distributed across multiple systems.

A user can enter commands and information into the computer 224 via an input device. Examples of such input devices include, but are not limited to, a keyboard, pointing device (e.g., a "mouse"), a microphone, a joystick, a serial port, a scanner, and the like. These and other input devices can be connected to the processing unit 226 via a human machine interface that is coupled to the system bus, but may be connected by other interface and bus structures, such as a parallel port, game port, or a universal serial bus (USB).

The computer 224 can operate in a networked environment using logical connections to one or more remote computing devices. By way of example, a remote computing device can be a personal computer, portable computer, a server, a router, a network computer, a peer device or other common network node, and so on. Logical connections between the computer 223 and a remote computing device can be made via a local area network (LAN) and a general wide area network (WAN). Such network connections can be through a network adapter. A network adapter can be implemented in both wired and wireless environments. Such networking environments are commonplace in offices, enterprise-wide computer networks, intranets, and the Internet.

An implementation of application software may be stored on or transmitted across some form of computer readable media. Computer readable media can be any available media that can be accessed by a computer. By way of example, and not limitation, computer readable media may comprise "computer storage media" and "communications media." "Computer storage media" include volatile and non-volatile, removable and non-removable media implemented in any method or technology for storage of information such as computer readable instructions, data structures, program modules, or other data.

Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer. An implementation of the disclosed method may be stored on or transmitted across some form of computer readable media.

The processing of the disclosed method can be performed by software components. The disclosed method may be described in the general context of computer-executable instructions, such as program modules, being executed by one or more computers or other devices. Generally, program modules include computer code, routines, programs, objects, components, data structures, etc. that perform particular tasks or implement particular abstract data types. The disclosed method may also be practiced in grid-based and distributed computing environments where tasks are performed by remote processing devices that are linked through a communications network. In a distributed computing environment, program modules may be located in both local and remote computer storage media including memory storage devices.

Although, the embodiments described above in relation to the system 200 and 300 can be used to cool or heat core temperature in accordance with aspects of the invention, it should be noted that features of these systems, including the computer 224, are optional. For example, a system for cooling core body temperature can include a heating element for heating skin or tissue of a subject that results in dilation of AVAs in glabrous skin. The system can further comprise a cooling device that provides a cooling stimulus to glabrous skin of a subject. Such a cooling device is optionally a cooled container of fluid, a cooled gel pack, an ice cube, or a cooled source of gas. Similarly, a device used to heat core temperature can comprise a heating element for heating skin or tissue of a subject that results in dilation of AVAs in glabrous skin. The system for heating can further comprise a heating device for providing a heating stimulus to glabrous skin of a subject.

Figure 4:
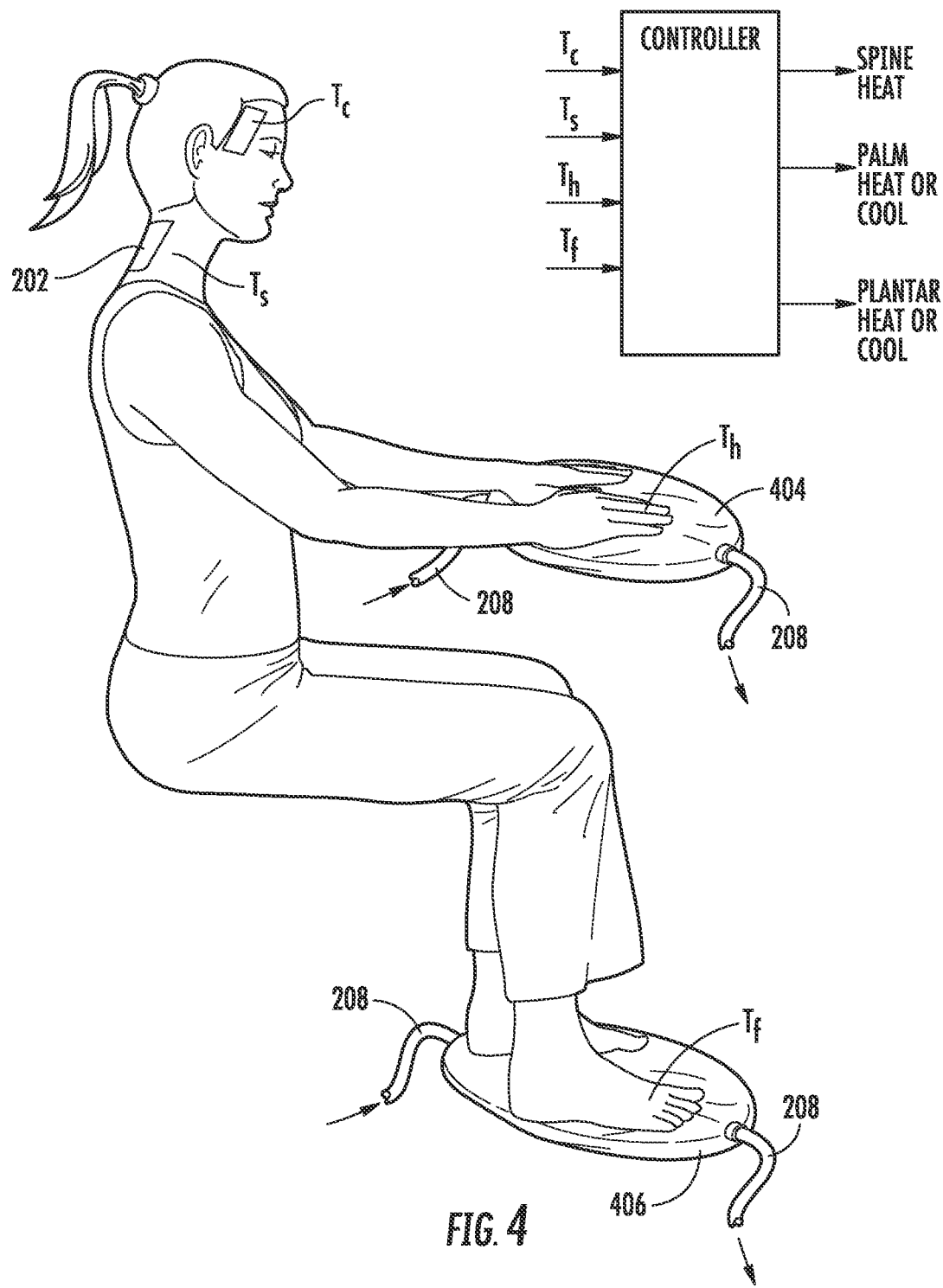
FIG. 4 is a schematic illustration showing aspects of an example system for cooling or heating the core temperature of a mammalian subject.

Referring now to FIG. 4 an example system is illustrated in which a controller is applied to coordinate the magnitudes of spine heating (Ts) and palmar (Th) heating or cooling and plantar (Tf) heating or cooling as functions of temperature inputs for the core (Tc), spine (Ts) and palmar (Th) and plantar (TO skin surfaces. A controller algorithm provides safety to the user and optimum thermal performance for applications in which the core temperature of the user is being manipulated.

Figure 6A:
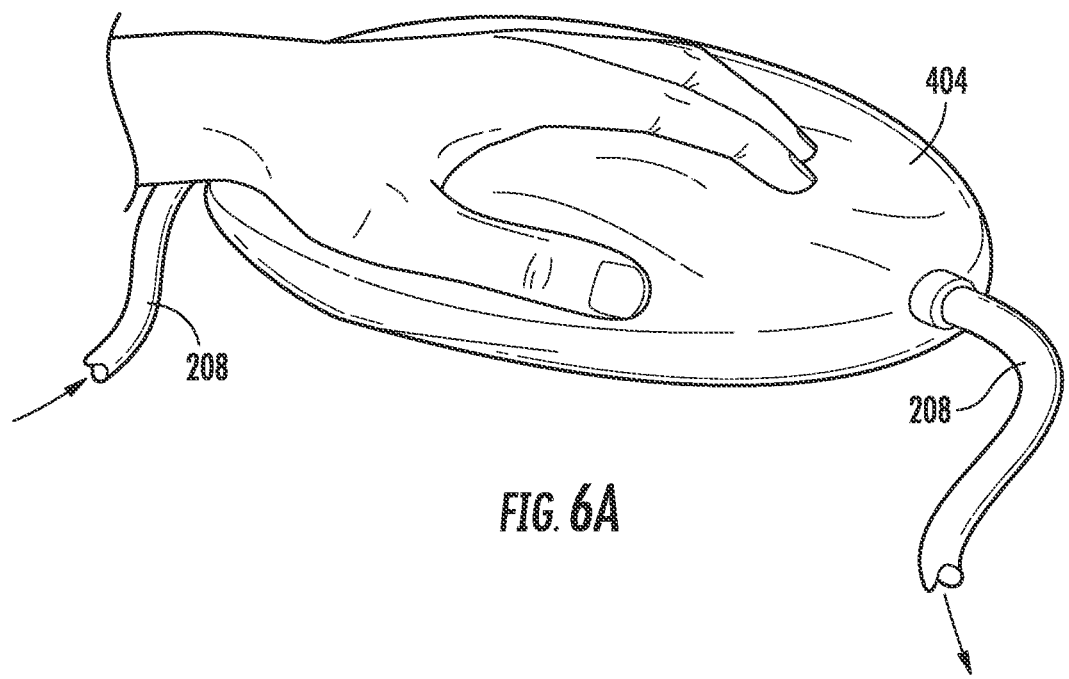
FIGS. 6A and 6B are schematic illustrations showing aspects of the example system of FIG. 4.

FIGS. 6A and B show example devices 404 and 406 for cooling or heating the palmar or plantar glabrous skin respectively. Such example devices can optionally used in the system 200 and 300 as system element 204. Optionally, 404 and 406 are used for cooling and a conduit 208 directs flow of cooled fluid or gas through the devices to provide a cooling stimulus to the palmar or plantar glabrous skin.

FIG. 6A illustrates methods and devices for heating or cooling the surface of glabrous palmar skin and ventral aspect of the fingers of the hand that contain arteriovenous anastomosis vascular structures can include establishing a contact area with a flexible hot or cold source bladder at a specified temperature through which flows a controlled temperature fluid via inlet and outlet ports thereby providing a thermal mechanism of adding or removing energy to or from the glabrous skin, according to a specific embodiment of the disclosure.

Figure 6B:
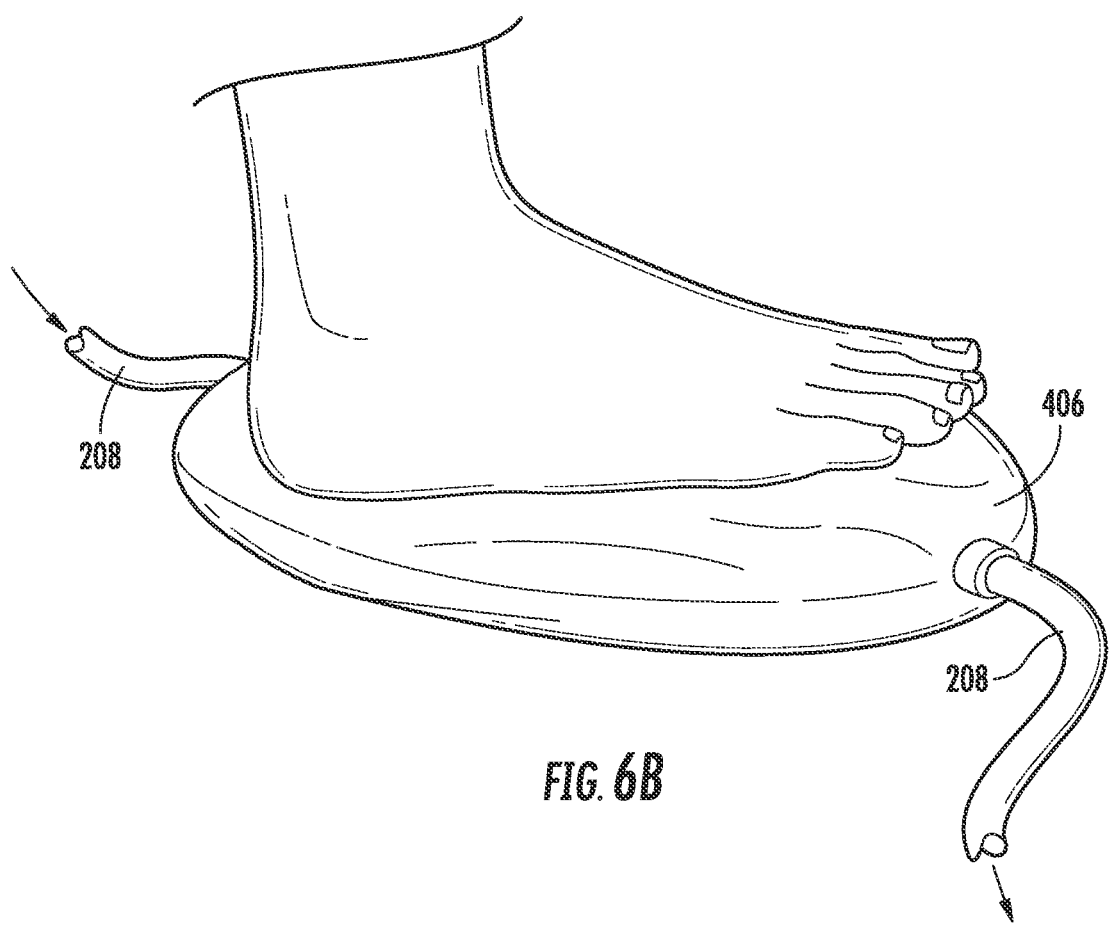

FIG. 6B illustrates methods and devices for heating or cooling the surface of glabrous plantar skin and ventral aspect of the toes of the foot that contain arteriovenous anastomosis vascular structures by establishing a contract area with a flexible hot or cold source bladder at a specified temperature through which flows a controlled temperature fluid via inlet and outlet ports thereby providing a thermal mechanism of adding or removing energy to or from the glabrous skin, according to a specific example embodiment of the disclosure.

As described with regard to the systems 200 and 300, according to some embodiments, the disclosed systems and methods may comprise applying a negative pressure to at least a portion of a subject's skin. For example, negative pressure may be applied to glabrous skin on the hands, feet and/or face. In some embodiments, a surface vacuum system may be maintained at a predetermined negative pressure until the warming or cooling is achieved, i.e. till the body core of a subject reaches the desired temperature.

Optionally, a chilled or warmed pack may be located peripherally to a vacuum chamber and glabrous skin where they cool or warm a liquid that is circulated under the action of a pump to a flexible bladder positioned in the interior of the vacuum chamber in contact with glabrous skin.

The negative pressure may optionally be up to about 25 mm Hg, up to about 50 mm Hg, up to about 75 mm Hg, and/or up to about 100 mm Hg. In some embodiments, the devices of the disclosure may produce negative pressure by a portable surface vacuum system that comprises a means for manual evacuation, for example, by a manual bulb pumping device or a manual lineal pumping device or a manual rotary pumping device or a manual hinged pumping device or a bellows pumping device or a self-contained battery operated vacuum pump.

A manual vacuum generating system may be operated by application of the motion of a hand, of both hands, of a foot, of both feet, of a combination of hands and feet, or by application of relative motion of other body members. The manual vacuum generating system may be operated by a single person or by the cooperation of multiple people.

A portable surface vacuum system comprises a vacuum pump that may be operably attached to an impermeable cover designed to cover only the glabrous skin surface which is being cooled or heated. An impermeable cover may comprise a suction port that is attached to a vacuum pump and a peripheral seal operable to seal in vacuum generated by the vacuum pump onto a glabrous skin surface of the body of the mammal. A surface vacuum system may also comprise a heating or a cooling means for delivering heat or cold to a glabrous surface.

Optionally, a portable surface vacuum system is used to apply negative pressure without insertion of a body appendage into a non-portable and/or rigid vacuum chamber. In these embodiments, the outer surface of the vacuum confining volume (i.e. vacuum chamber or negative pressure chamber) may be made with an impermeable flexible material. A cooling or warming pack may be placed against glabrous skin at a site of treatment prior to being covered with such an impermeable flexible material. The impermeable flexible material may be sealed against the glabrous skin around its periphery. A port placed in the impermeable flexible material provides a connection to a vacuum generating device so that the volume interior to the sealed perimeter may be evacuated to desired level of negative pressure. When a vacuum is created therein the action of atmospheric pressure on the outer surface of the impermeable flexible material translates a mechanical force onto a heating pack or a cooling pack placed against the glabrous skin on the interior, increasing the pressure of the pack onto the skin, thereby reducing the thermal resistance between the pack and the skin and producing more effective heat transfer between the pack and the skin.

In other embodiments, a portable surface vacuum system of the disclosure allows for application of negative pressure by insertion of a body appendage into a portable rigid vacuum chamber. A rigid chamber does not substantially change its shape when a vacuum is created on the interior. A rigid chamber incorporates a sealing element at the location where a body appendage is inserted into the chamber so that a seal is created around the perimeter of the appendage to support and maintain a negative pressure on the interior of the chamber.

In some embodiments, a rigid chamber of a portable vacuum device of the disclosure, may have a second opening with a sealing cover having a size sufficient to permit insertion of a cooling or warming pack and for an operator to position said pack in contact with the body appendage of the treatment subject.

The sealing cover may be opened and closed easily and quickly, and in the closed position it supports the generation of a negative pressure in the interior of the rigid chamber. The sealing cover may be opened and closed by pivoting on hinges or by turning screw threads or by loosening and fastening latches. A sealing medium is placed between the mating surfaces of the cover and the rigid chamber to block the flow of air when a negative pressure is generated interior to the rigid chamber. The rigid chamber may have a mechanical vacuum gauge installed to enable an operator to monitor the state of vacuum.

In some embodiments, the surface vacuum system may cover about 50 mm$^2$ or less of glabrous skin. Other embodiments may cover up to about 500 mm$^2$ of glabrous skin. In some applications multiple areas of glabrous skin may be treated simultaneously so that the total treatment area is additive of the individual areas. The actual treatment area may vary widely depending on the area of the body having glabrous skin that is selected for the process, the number of sites, and the overall size of the subject.

Figure 7:
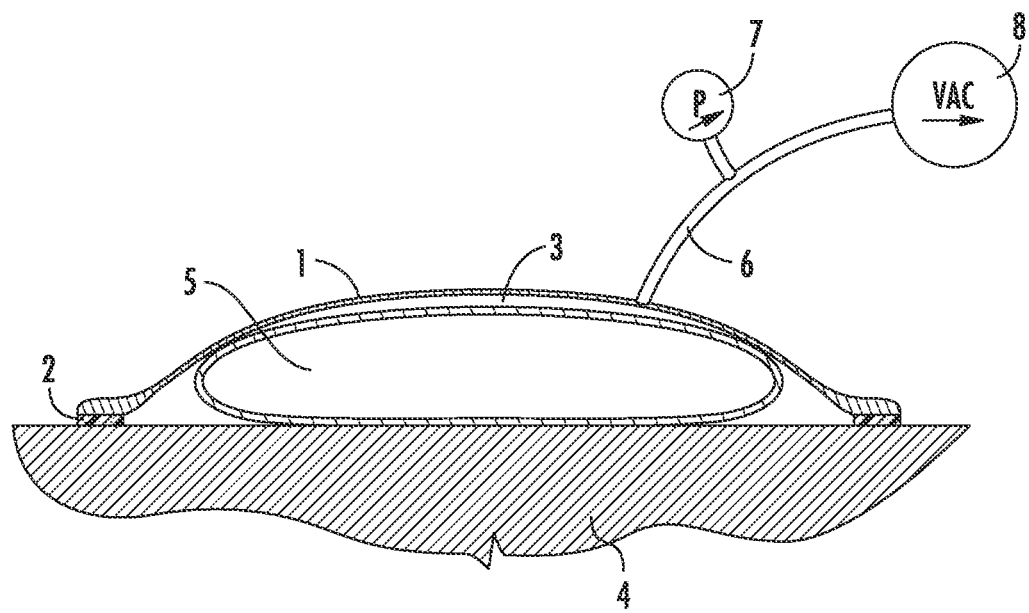
FIG. 7 is a schematic illustration of aspects of a system for altering temperature in a mammalian body.

Referring now to FIGS. 7-14, example devices for use with the described systems and methods are provided. FIG. 7 illustrates a cross sectional view of a portable negative pressure device comprising a warming or cooling pack 5 in contact with the surface of glabrous skin 4. A flexible impermeable cover 1 is positioned over the application area with a seal 2 around the perimeter. A negative pressure 3 interior to the cover is formed and applied to the glabrous skin. A gauge 7 can be used to monitor the level of negative pressure, and a source of pumping 8 (vacuum) with a connection 6 to the interior of the impermeable cover is used to generate the negative pressure therein. The device shown in FIG. 7 can, for example, be used as the glabrous skin cooling device 204 of systems 200 and 300.

Figure 8:
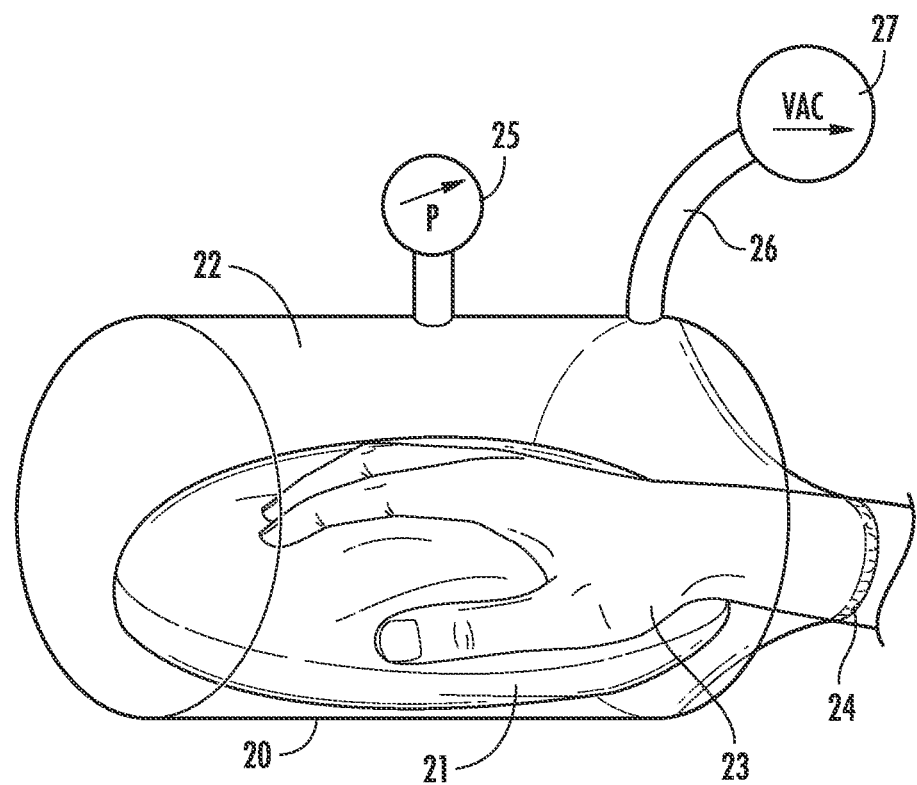
FIG. 8 is a schematic illustration of aspects of a system for altering temperature in a mammalian body.

FIG. 8 illustrates a negative pressure device including a portable surface vacuum device having a rigid vessel 20 into which an appendage of a body 23 may be inserted with a pressure seal 24 circumferentially on the skin at the point of insertion. A warming or cooling pack 21 is positioned in contact with the surface of glabrous skin under conditions of negative pressure on the interior of the vessel. A source is provided for generating a negative pressure 27 inside the vessel 20 and connected 26 to the vessel interior and a gauge 25 is used for monitoring the degree of negative pressure. The device shown in FIG. 8 can, for example, be used as the glabrous skin cooling device 204 of systems 200 and 300.

Figure 9:
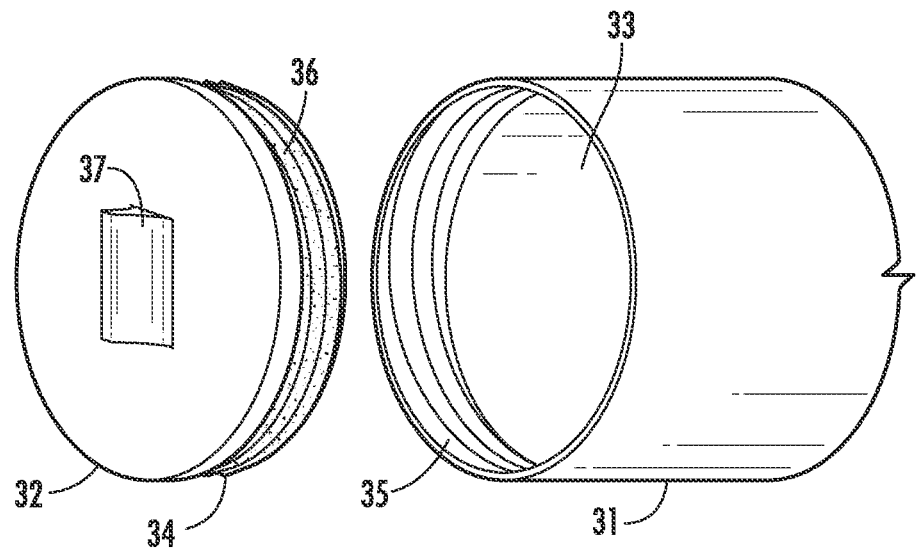
FIG. 9 is a schematic illustration of aspects of a system for altering temperature in a mammalian body.

FIG. 9 illustrates a portable negative pressure device including a rigid vessel/chamber 31 into which an appendage of a body may be inserted with a pressure seal circumferentially on the skin at the point of insertion. A second opening 33 through which a warming or cooling pack may be inserted can be in contact with the surface of glabrous skin under conditions of negative pressure on the interior of the vessel. The second opening can be opened and closed by rotating a removable element 32 having male screw threads 34 that match female threads 35 on an opening in the rigid vessel. A sealing substance such as Teflon tape 36 is optionally applied to the screw threads to provide a seal between the second removable element and the rigid container when the second element is attached so as to contain the negative pressure interior to the rigid vessel. The removable element has an appendage 37 that can be grasped to rotate the element for installing or removing the element from the rigid vessel of the portable surface vacuum chamber. The device shown in FIG. 9 can, for example, be used as the glabrous skin cooling device 204 of systems 200 and 300.

Figure 10:
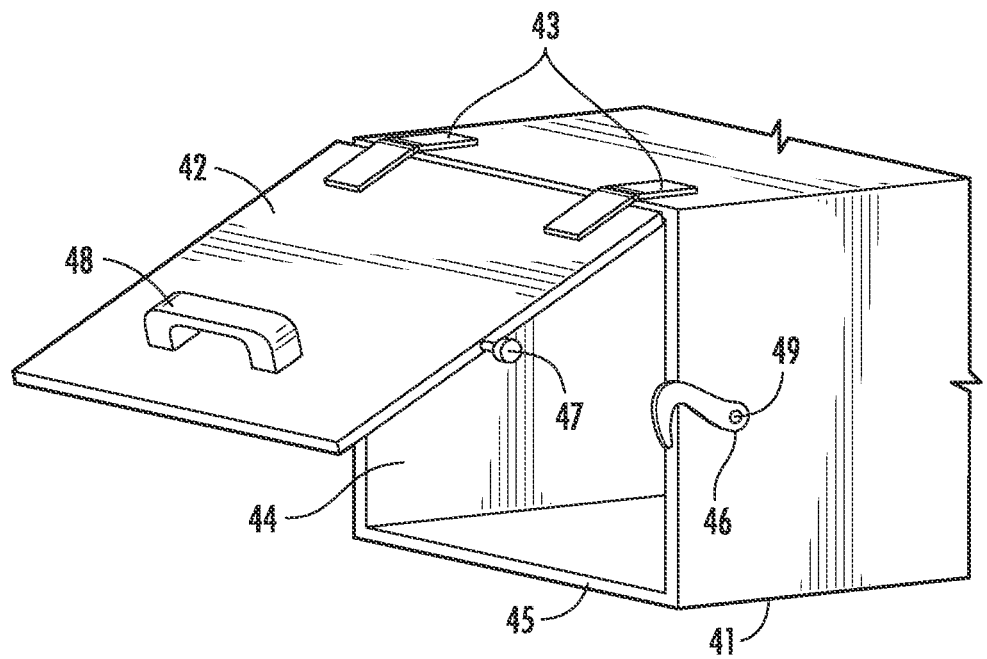
FIG. 10 is a schematic illustration of aspects of a system for altering temperature in a mammalian body.

FIG. 10 illustrates a negative pressure device including a portable surface vacuum chamber having a rigid vessel 41 into which an appendage of a body may be inserted with a pressure seal circumferentially on the skin at the point of insertion. The device further comprises a second opening 44 through which a warming or cooling pack may be inserted to be in contact with the surface of glabrous skin under conditions of negative pressure on the interior of the vessel. The second opening can be opened and closed by pivoting a second element 42 attached by one of more hinges 43 to a portion of the perimeter of the opening in the rigid vessel. One or more latches 46 mounted on a pivot 49 and matching pins 47 or other locking devices are used to secure the second element in a sealed position against the second opening in the rigid vessel. A sealing substance such as Teflon tape is optionally applied to the mating surfaces 45 of the rigid vessel and/or second element to provide a seal between the second hinged element and the rigid container when the second element is rotated to a closed position against the rigid vessel so as to contain the negative pressure interior to the rigid vessel. A handle 48 is provided to open and close the second element. The device shown in FIG. 10 can, for example, be used as the glabrous skin cooling device 204 of systems 200 and 300.

Figure 11:
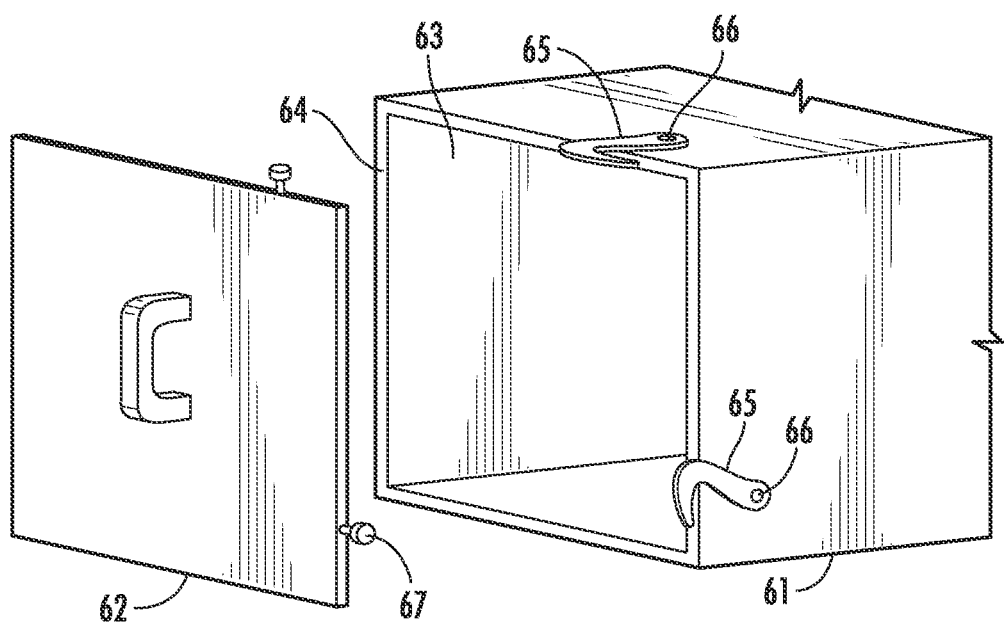
FIG. 11 is a schematic illustration of aspects of a system for altering temperature in a mammalian body.

FIG. 11 illustrates a negative pressure device including a portable vacuum chamber having a rigid vessel 61 into which an appendage of a body may be inserted with a pressure seal circumferentially on the skin at the point of insertion. The device includes a second opening 63 through which a warming or cooling pack may be inserted to be in contact with the surface of glabrous skin under conditions of negative pressure on the interior of the vessel. The second opening can be opened and closed by removal a second element 62 that is shaped to match the opening in the rigid vessel. One or more latches 65 is mounted on a pivot 66 and matching pins 67 or other locking devices are used to secure the second element in a sealed position against the second opening in the rigid vessel. A sealing substance such as Teflon tape is optionally applied to the mating surfaces 64 of the rigid vessel and/or second element to provide a seal between the second element and the rigid container when the second element is positioned to a closed position against the rigid vessel so as to contain the negative pressure interior to the rigid vessel. The device shown in FIG. 11 can, for example, be used as the glabrous skin cooling device 204 of systems 200 and 300.

Figure 12:
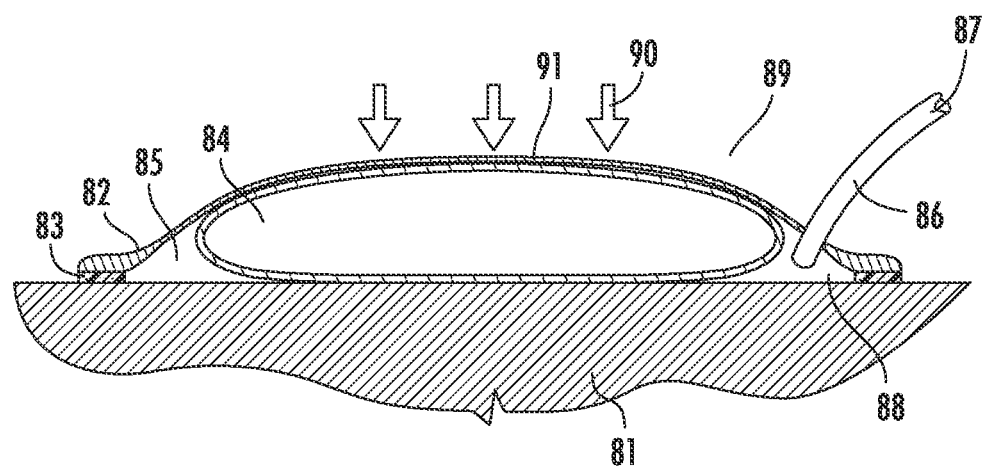
FIG. 12 is a schematic illustration of aspects of a system for altering temperature in a mammalian body.

FIG. 12 illustrates a negative pressure device vacuum generating device. The device includes an impermeable cover 91 operably attached 86 to the vacuum generating device 87 to produce a negative pressure on the interior 88 of the impermeable cover. The impermeable cover is operable to cover a glabrous skin surface 81. The impermeable cover has a sealing means 83 to seal a perimeter area of the glabrous skin. The impermeable cover encloses a flexible cooling or warming pack 84 in its interior and positioned against glabrous skin so that it may exchange heat with the skin. The impermeable cover is optionally flexible so that the combined actions of the higher exterior pressure 89 and the lower interior pressure 85 when applied across the surface area 82 of the impermeable cover results in a mechanical force 90 applied onto the flexible cooling or heating pack to force it against the glabrous skin providing a reduced thermal contact resistance at the interface and improved heat transfer between the pack and the glabrous skin. The device shown in FIG. 12 can, for example, be used as the glabrous skin cooling device 204 of systems 200 and 300.

Figure 13:
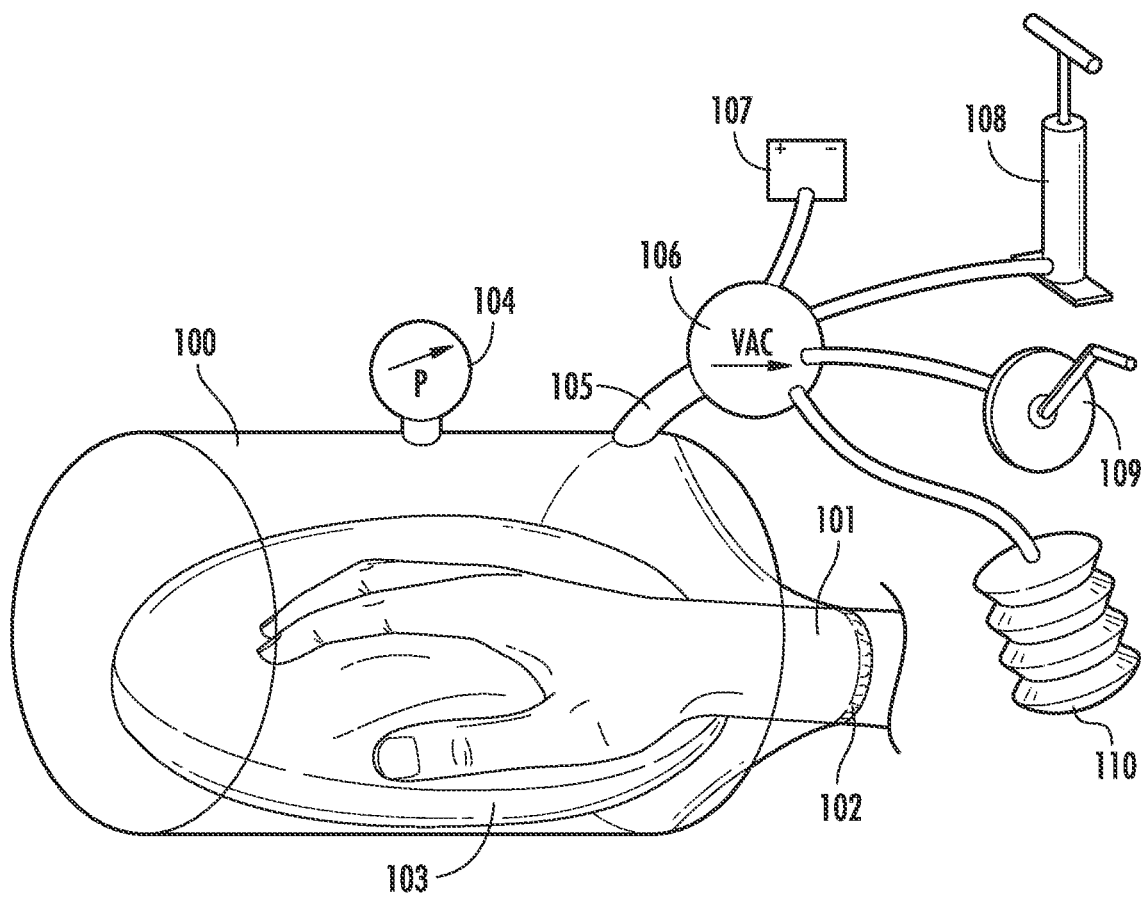
FIG. 13 is a schematic illustration of aspects of a system for altering temperature in a mammalian body.

FIG. 13 illustrates a negative pressure volume containment device 100 which may be applied to seal a defined area of glabrous skin and into which may be placed a cooling or warming pack 103 to transfer heat from or to the skin. A peripheral seal 102 is formed around the body appendage 101 containing glabrous skin. A pressure monitoring device 104 is used to continuously measure the pressure within the negative pressure device. The device also includes a connection 105 to a vacuum generating source 106 which is operable in the absence of external power sources. Operation may be by manual means such as manual compression of a confined volume (a bellows or a bulb or other flexible compression device 110), a linear pumping motion 108, a rotary pumping motion 109, or by a powered means in which a portable self-contained energy source 107 such as a battery drives a vacuum pump. The device shown in FIG. 13 can, for example, be used as the glabrous skin cooling device 204 of systems 200 and 300.

Figure 14:
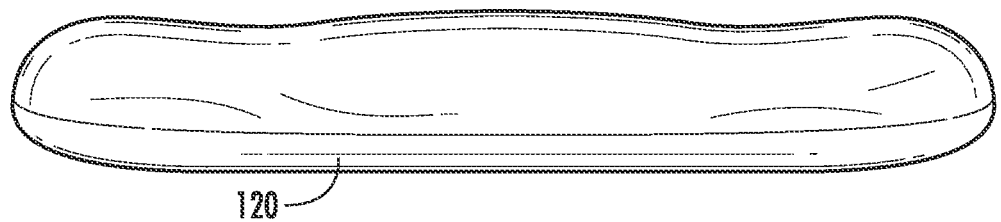
FIG. 14 is a schematic illustration of aspects of a system for altering temperature in a mammalian body.

FIG. 14 illustrates a flexible cooling or warming pack 120 that may be inserted into the interior of a negative pressure volume as shown in the prior figures to contact and conform to the topology of glabrous skin of a mammal while transferring heat to or from the skin. The pack may be brought to a desired treatment temperature by pre-cooling or pre-heating, by mixing contained chemical components previously separated by barriers that may be ruptured at the time of treatment to allow an endothermic or exothermic mixing process, or by exposing contained chemical components to air causing an exothermic reaction after the pack is removed from an initially sealed container, according to a specific example of the disclosure.

As described throughout, control of blood flow through the arteriovenous anastomoses of the skin is critical to thermoregulatory function. The ability to manipulate blood flow through the AVAs, especially from an incipient state of vasoconstriction, holds important consequences for medical applications that involve the modulation of core body temperature and for alleviating issues of personal thermal discomfort.

Described herein are methods, processes, systems and devices for accomplishing on demand increases in the flow of blood through the AVAs and thereby the ability to raise or lower the body core temperature. In some embodiments, arteriovenous anastomoses (AVAs), may be dilated and/or distended. Without limiting any specific embodiment to any particular mechanism of action, dilating and/or distending AVAs may cause diversion of a large fraction of cardiac output to the skin. The skin may mediate heat exchange with the environment which may then be convected to the body thermal core. In some embodiments, the rate of core temperature change may be ten times faster than possible using existing conventional methods and devices in the absence of AVA vasodilation and/or distention enhancements.

The described systems and methods can be used to cool and/or heat the core temperature of a mammal that may or may not initially be vasoconstricted. In conjunction with thermal stimulation of peripheral sites of thermoregulatory control to produce greater blood perfusion to glabrous skin, the surface of glabrous skin may be heated or cooled to respectively add or remove heat from blood circulating from the body core. The disclosed methods and devices are capable of increasing on demand the convective flow of heat between the skin surface and the body core via the circulation of blood. The methods and devices may be applied to lower the body core temperature from a normothermic state to produce a state of hypothermia, and from a hyperthermic state toward a normothermic state, and to increase the body core temperature from a hypothermic state toward a normothermic state, and from a normothermic state to a hyperthermic state. An example application of the latter process could be instances where it is desirable to create an artificial febrile state to enhance cancer therapies.

For some embodiments in which the AVAs are initially in at least a partial state of vasoconstriction, the vasoconstriction action of the AVAs is relaxed or reduced at least in part by the method of heating thermal receptors in the thermoregulatory control center peripheral to the brain so as to stimulate the requisite input signals to reduce vasoconstriction in the AVAs. The result of increased AVA vasodilation is greatly decreased flow resistance of the AVAs such that there is a diversion of a larger fraction of the cardiac output to the AVAs.

As a consequence of the increased blood flow through the AVAs, the glabrous skin will be warmed by the greater convective heat transfer with blood flowing from the warmer body core. The described systems and methods can implement various specific devices and processes for heating to thermally stimulate peripheral thermoregulatory control tissue that cause the process of warming glabrous skin via increased convective heat exchange with warm core blood.

As a further consequence of the increased blood flow through the AVAs, the glabrous skin can be used as a heat transfer medium between heating or cooling sources applied to its surface and blood flowing through the AVAs. The process creates the opportunity to adjust the temperature of a fraction of the cardiac output which is circulated back to the body core, with minimal heat exchange in the intermediate larger diameter and higher velocity vessels, until it equilibrates thermally with the total blood volume and tissues of the body core, thereby providing a direct transport link to externally modulate the body core temperature.

The described systems and methods can be used to rapidly increase or decrease the core body temperature of a mammalian body for therapeutic and other uses. For example, induction of hypothermia provides protection to the brain from ischemic events in subjects that may have suffered impairments such as cardiopulmonary arrest, ischemic stroke, subarachnoid hemorrhage, hepatic encephalopathy, perinatal asphyxia, infantile viral encephalitis, or an acute traumatic brain injury.

The described systems and methods may be used to cool the body of a user in response to a hyperthermia-inducing activity or event. Some non-limiting examples of hyperthermia-inducing activities include endurance-limited activities such as athletic performance, and/or working in an environment of high heat (mining industry, construction industry, forestry industry, metals processing industry), and/or exposure to an environment of high heat stress, and/or military operations. The described systems and methods may also be used to ameliorate or eliminate the effects of warming of the body temperature to mortally dangerous temperatures higher than the normal operating range.

The described systems and methods may be used to warm the body of a human user in response to a hypothermia-inducing activity or event. Some non-limiting examples of hypothermia-inducing activities include working in extremely cold environments, and/or extended exposure to a very cold environment, particularly in the absence of a significant level of physical activity, and/or prolonged exposure to water, and/or prolonged athletic activities in cold/water-based environments, and/or being seated in a vehicle under cold conditions. The described systems and methods may be used to ameliorate or eliminate the effects of excessive cooling of the body core temperature that may lead to injury and/or death.

The described systems and methods may safely extend the performance envelope for any of the foregoing types of activities and/or safely extend the period of exposure to the extreme temperature by adjusting the temperature of the body core. In some embodiments, the user may continue to engage in the activity or continue to be exposed to the extreme temperature as mobility of the user is not hindered.

The described systems and methods may be used to induce a state of mild hypothermia of up to 2° C. without any techniques that are invasive to the skin surface and/or that require sterile conditions and/or that require access to central electrical power. In some embodiments the device or method of the disclosure can be practiced by personnel with a level of training commensurate with EMS medical personnel and in field conditions without access to central electrical power.

The described systems and methods may be used to induce therapeutic hypothermia for subjects or people at risk of ischemic injury. For example, localized heating may be applied to a peripheral site of thermoregulatory control to cause relaxation of arteriovenous anastomosis vasoconstriction to produce greater blood perfusion of glabrous skin that can then be locally cooled to enhance convective heat transfer in the skin to produce rapid cooling of the body thermal core to a state of therapeutic hypothermia. This may be used to provide treatment or neuroprotection for medical cases such as cardiac arrest, stroke, traumatic brain injury, vasculature surgery, neonatal brain injury and combinations thereof.

Optionally, the systems, devices and methods can be operated or performed without external AC electrical power sources. It may be possible to attach the system or a portion of the systems described to a stationary electrical power source operating an electrically driven vacuum pump for applications in which the device is positioned within physical access of such power sources.

Optionally, the described systems and devices are portable. In some embodiments, a device of the disclosure may be light-weight. Portability and/or the ability to operate without an external AC electrical power source and/or light-weight may provide operational functionality in some applications. For example, portability and/or light-weight provide an advantage for use in an EMS vehicle, in a medical helicopter, in a commercial airliner, in a military operational vehicle, at an industrial work site, a sports playing field, and a remote activity venue. The portability and light-weight may make the device desirable to carry on space craft or an aircraft to provide immediate life saving treatment to a subject who suffers an ischemic event. Optionally, the systems and device may be sufficiently compact to be placed and carried in a first aid kit.

In some embodiments, use of a surface vacuum system to apply negative pressure to a portion of a glabrous skin surface removes the necessity of inserting an appendage comprising glabrous skin into a rigid vacuum container.

The systems and devices of the disclosure may be completely portable and require no external AC electrical power sources rendering them usable in critical medical care situations such at the site of an injury or road accident, or while being carried on an ambulance or helicopter to provide important rapid cooling therapy for victims of cardiac arrest, stroke, traumatic head injury, or neonatal brain injuries or impairment to provide protection from possible ischemic injury. The present disclosure, in some embodiments, relates to portable heating or cooling devices, methods of inducing flow of blood to the AVAs when it is initially not active, and methods to regulate and/or adjust and/or modify the body core temperature while allowing mobility, e.g. complete mobility, for the user.

Optionally, the surface of glabrous skin may be heated or cooled so as to modulate the body core temperature without adversely affecting enhanced AVA blood flow and for implementation in a wide diversity of venues and circumstances where the medical benefits of adjusting the body core temperature may be desired. Of note, the latter venues and circumstance may include producing a state of mild hypothermia shortly following an ischemia producing event in a location remote from a medical care facility.

The systems or devices of can be optionally attached to a stationary electrical power source operating an electrically driven heat transfer fluid pump and refrigeration system for applications in which the device is positioned within physical access of such power sources. In some embodiments, a device of the disclosure may be portable.

The present disclosure provides methods and devices that can elicit blood perfusion to the AVAs in glabrous skin via focal thermal stimulation to key sites of peripheral thermoregulatory control. Thermal stimulation to sites of peripheral thermoregulatory control having parasympathetic innervation sends signals to AVAs in glabrous skin that cause vasoconstriction to relax, producing increased blood flow to glabrous skin. One outcome of this stimulation is that in the absence of local heating or cooling the glabrous skin will be warmed from the former state of vasoconstriction. This outcome can be used to benefit in instances wherein warming of the hands and/or feet will cause an increase in the state of thermal comfort.

One application of this process is to incorporate the thermal stimulation into the upper seat back of a vehicle whereby the cervical spine can be heated in order to enhance the comfort of occupants when the environmental temperature is low enough to cause discomfort. Additional applications include maintaining warmth of the palmar and plantar skin for situations in which is a person is exposed to a cold environment in combination with a low level of physical activity over an extended period of time, such watching an athletic event, waiting in a hunting blind, recording observations of the heavens, and innumerable other situations. The invention can be used in a residential setting for any conditions in which the hands and feet become uncomfortably cold and during any time of day or night. Medical applications may include the warming of patients who are uncomfortably cold. It may be combined with warming of the glabrous skin surfaces to add heat to blood circulated through the AVAs so as to circulate heat to the body core to warm it from a state of hypothermia as may be required.

Thermal stimulation may be induced by various means, including direct contact of the skin with a heated surface, directing a flow of warm air onto the stimulation site, and/or applying surface and/or penetrating electromagnetic energy at controlled wavelengths and intensity. Different means of thermal stimulation can alter the process time to diminish vasoconstriction of AVAs in order to match requirements for achieving comfort or medical benefit. The intensity of thermal stimulation may be regulated via a feedback control loop in order to ensure safety against causing thermal injury during stimulation and to provide optimal control of AVA vasodilation.

The physiological mechanisms that govern heat transfer between glabrous skin and the body core via convective blood flow through the AVAs as enhanced by application of spinal heating to relax vasoconstriction of AVAs and by application of negative pressure to glabrous skin to distend AVAs were evaluated.

Example 1

The application of negative pressure to glabrous skin was used to cause a significant increase in the flow of blood through the AVA vascular structure and the associated retia venosa. A laser Doppler flow probe was used to measure the change in blood flow in glabrous skin as a function of the magnitude of applied negative pressure.

A human hand was placed into a sealed rigid vacuum chamber on which was mounted an electronic negative pressure gauge. An optical laser Doppler flow probe was mounted onto the skin of the most distal pad of the middle finger to monitor blood flow continuously. The finger was exposed to ambient temperature air with no active cooling or warming applied to the skin. Control measurements were made with no negative pressure applied following an initial acclimatization period. The negative pressure was increased to a predetermined level and held for 15 minutes, then returned to zero.

Figure 15:
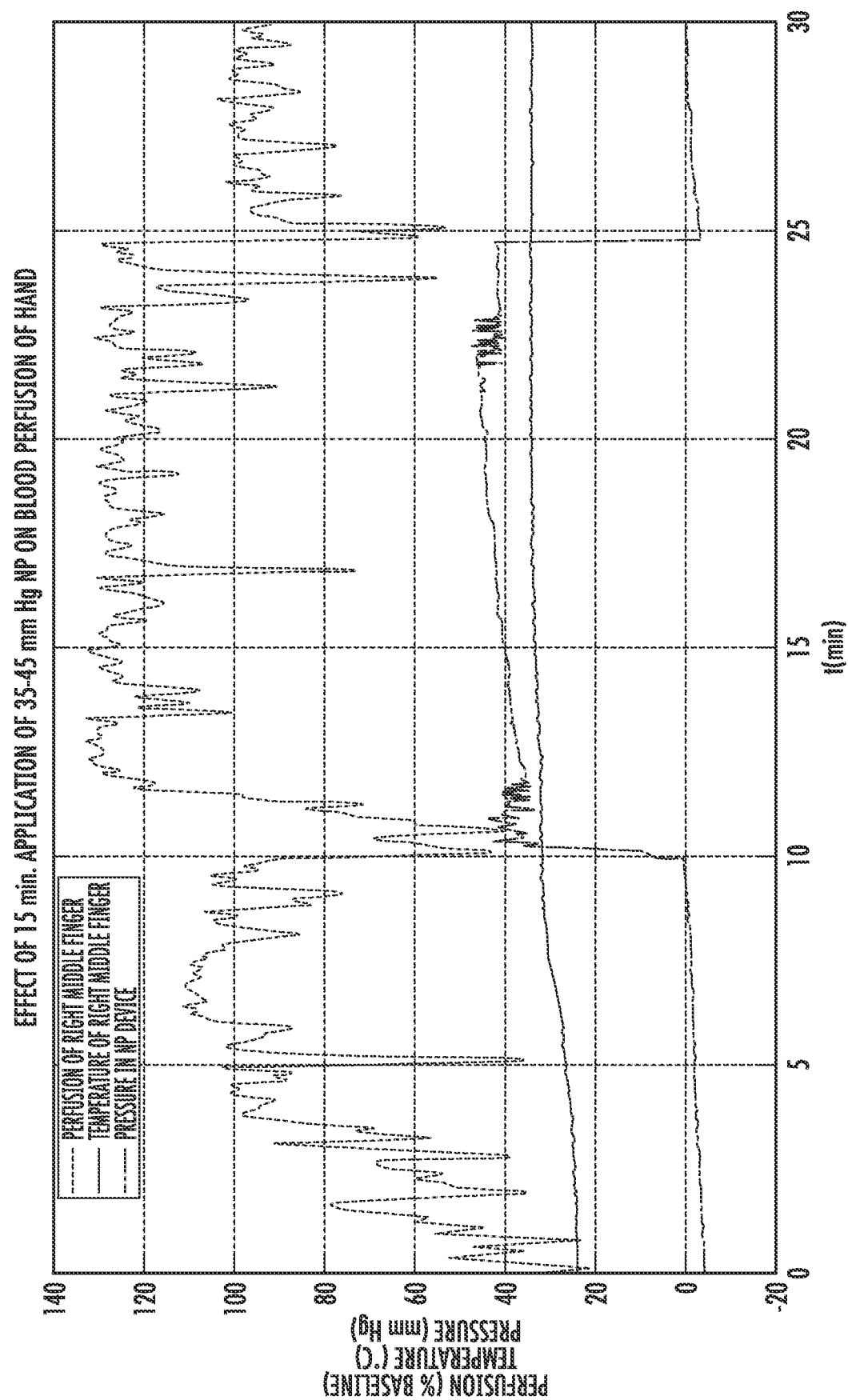
FIG. 15 is a graph showing the effect of application of negative pressure on blood perfusion in a hand.

Data from a sample protocol at a negative pressure of approximately 40 mm Hg is shown in FIG. 15. FIG. 15 depicts a blood flow plot and illustrates transient variation that is typical of AVA vasoactivity as the lumen diameter changes with time and thereby alters both flow impedance and velocity. Several features regarding the mechanistic basis of this physiological phenomenon are reflected in the data. For example, firstly under the action of negative pressure the average blood perfusion rate increases by approximately 30%, which is important for negative pressure technology function. Secondly, there is a sharp transient vasoconstriction of the AVAs in conjunction with major changes in the applied negative pressure, regardless of whether the change in pressure is positive or negative. This sympathetic driven behavior is a typical response to a sudden environmental input to the body. Third, after the negative pressure is removed the perfusion rate returns to approximately the level prior to the application of negative pressure. This behavior points to a direct cause and effect relationship between the increase in perfusion and applied negative pressure. Fourth, there is a large increase in perfusion by a factor of approximately three during the initial acclimatization period from an initial native state of AVA vasoconstriction.

Figure 16:
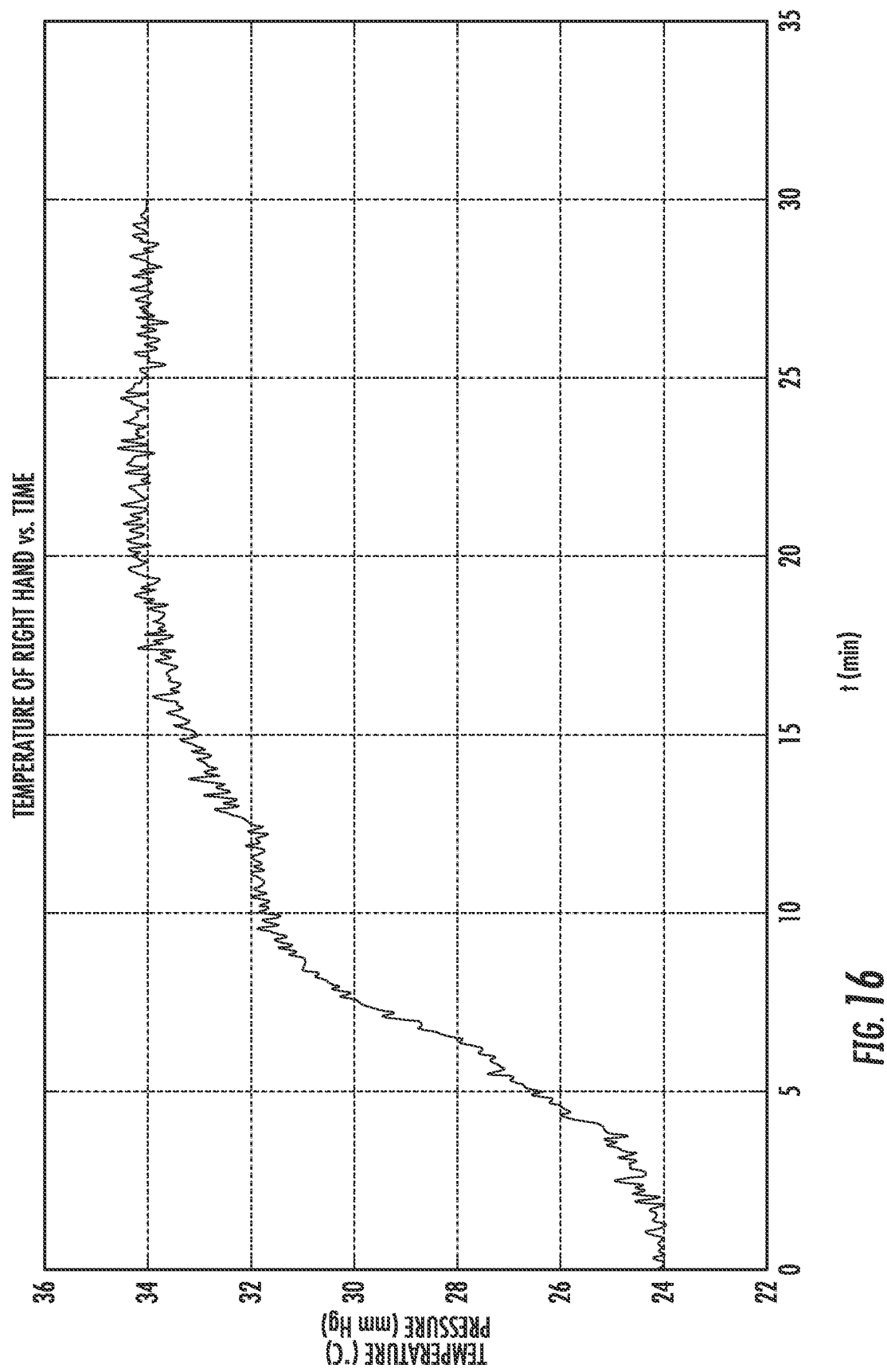
FIG. 16 is a graph showing the temperature of a hand over time.

The laser Doppler probe was also used to measure the skin surface temperature at the site of the perfusion measurement. FIG. 16 illustrates the temperature history during this experiment. At the start of the experiment, initial temperature of the skin was 24° C., which is indicative of a vasoconstricted state as is confirmed by the correspondingly low value of AVA perfusion. FIG. 15 shows a steady transition in blood flow over the first 11 minutes in the absence of negative pressure to a vasodilated state. FIG. 16 documents a corresponding rise in the skin temperature by approximately 8° C. to a new equilibrium value as the increased flow of warm blood from the body core through the AVAs caused an interior convective source that translated to the progressive warming of the skin surface. This data shows the coupling between AVA perfusion level and skin heat transfer and temperature.

FIG. 15 further shows the application of negative pressure at 11 minutes with a commensurate increase in AVA perfusion. A higher perfusion rate translates into a greater convection effect between warm blood and the skin tissue, issuing in a further increment in surface temperature. FIG. 16 documents the further increment in surface temperature by 2° C. as a result of the application of negative pressure. The net increase in surface temperature of the skin was 10° C. as a result of the increase in AVA perfusion. The two steps of temperature increments correspond to the two steps in perfusion increment, demonstrating mechanistic coupling of the two phenomena. The mechanistic action of blood perfusion on convective heat transfer in the glabrous skin is verified by these data.

Example 2

Figure 17:
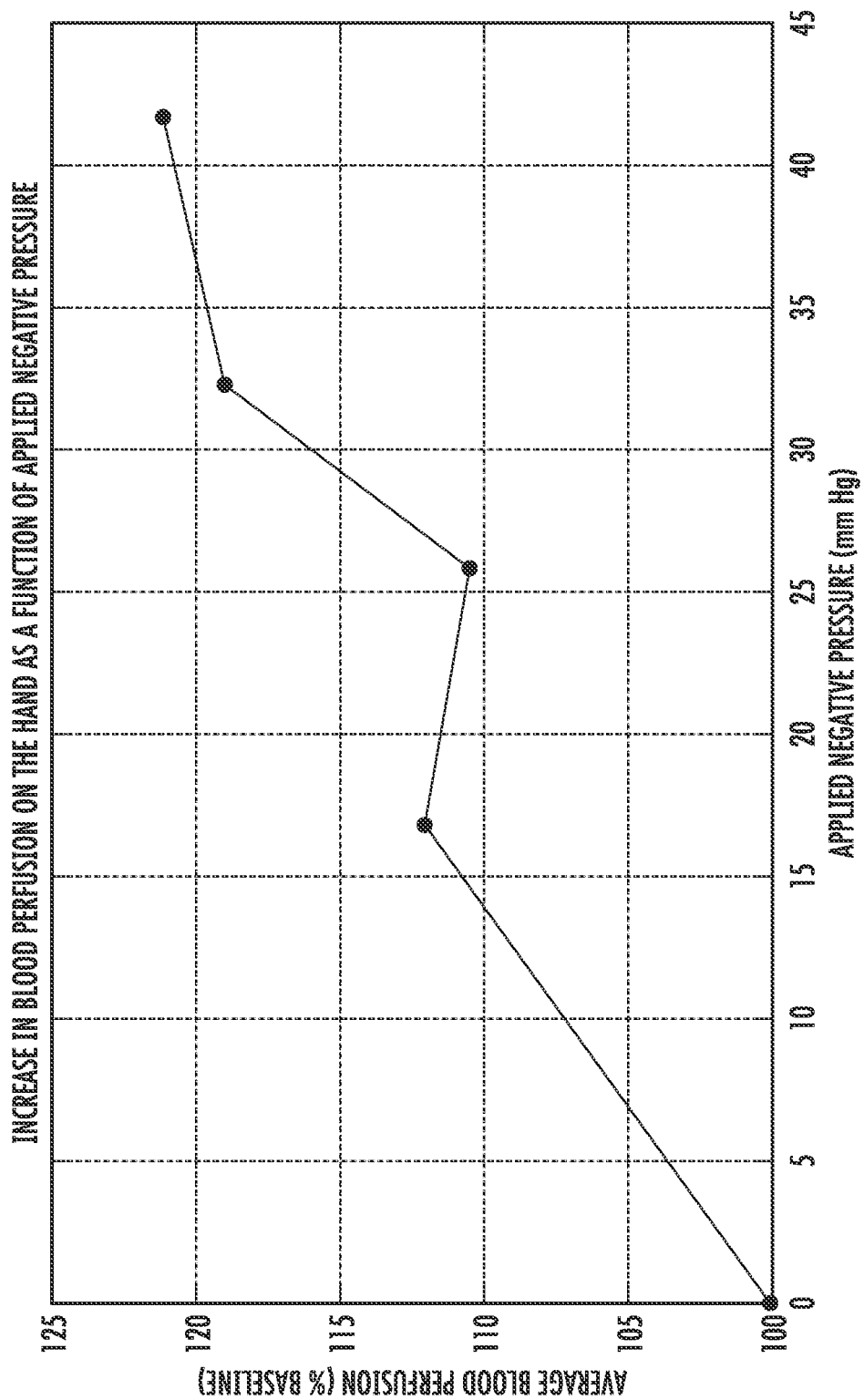
FIG. 17 is a graph showing increase in blood perfusion in a hand as a function of applied negative pressure.

A series of tests, similar to those described above and shown in FIG. 15, were conducted, each at a different value of negative pressure. The objective was to determine whether there is a proportional relationship between the magnitude of increase in perfusion and the magnitude of the applied negative pressure. Results of these experiments are shown in FIG. 17 which illustrates increments in blood perfusion measured by laser Doppler velocimetry on the most distal pad of the middle finger when exposed to various (graded) negative pressure values at room temperature air.

These data document a clear proportional relationship between applied negative pressure and the resulting increase in AVA perfusion. The mechanistic action of negative pressure on blood perfusion in the subject technology is verified by these data.

Example 3

The palm surface of the hand was subjected to cooling by contacting it with a flexible bladder through which chilled water was circulated at the same time that negative pressure was applied interior to a rigid chamber. A heat flux gauge and thermocouple were affixed to the palm in an area where it contacted the bladder. The protocol consisted of an equilibration period at room temperature, followed sequentially by the application of negative pressure, then bladder perfusion with water at 17° C., then cessation of negative pressure, reestablishment of negative pressure, and a final cessation of negative pressure.

Figure 18:
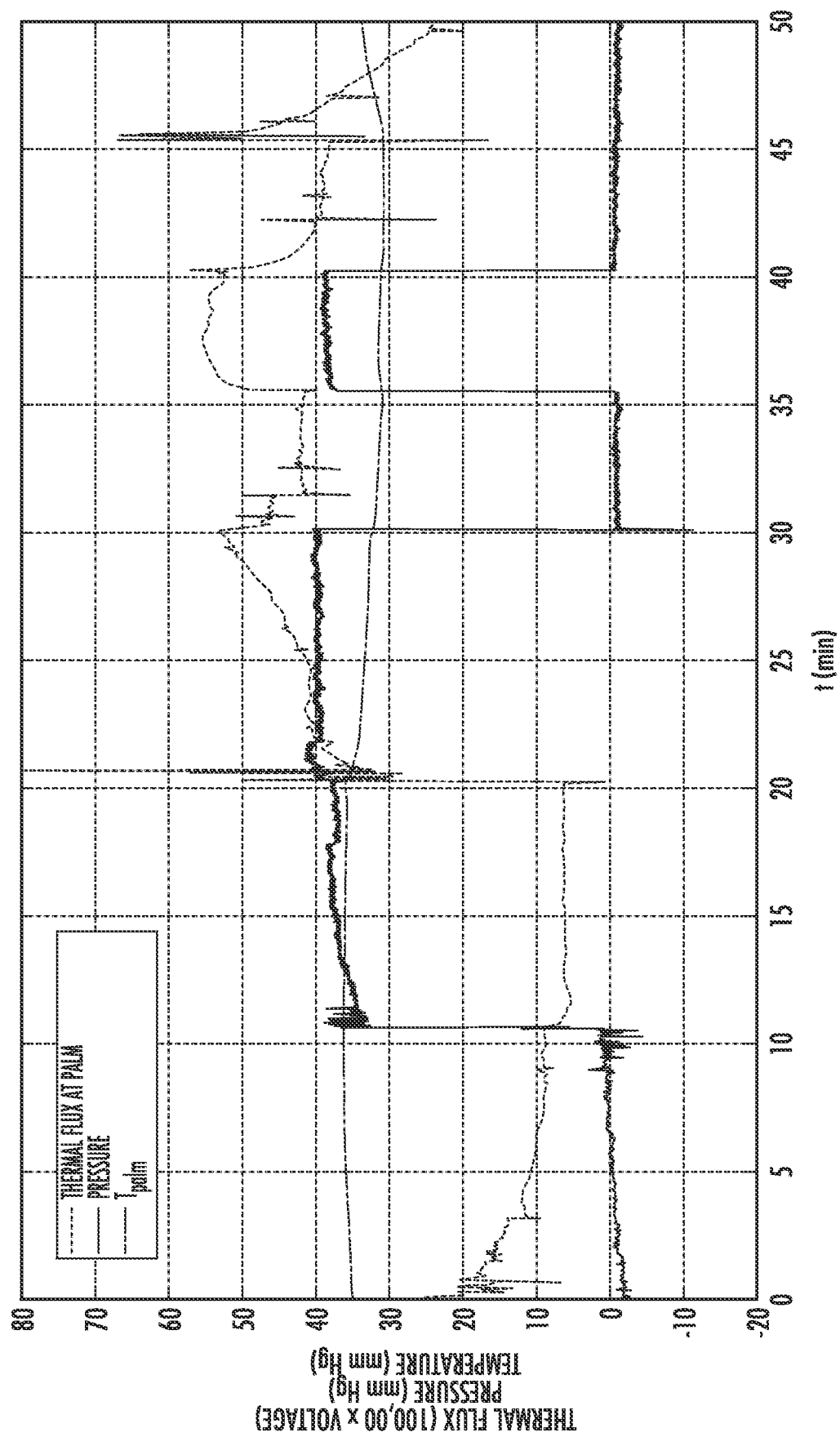
FIG. 18 is a graph showing thermal flux, pressure and temperature over time.

FIG. 18 shows data from this experiment in which water having a temperature of 23° C. was circulated through a bladder in contact with the palm of the hand. A significant enhancement in skin heat flux occurred (most upper lines of FIG. 18) when negative pressure (most lower lines of FIG. 18) was applied, which diminished when the negative pressure was removed. The temperature of the skin at the site of heat flux measurement is shown as the least variant plot.

After an eleven (11) minute equilibration period, negative pressure was increased to 40 mm Hg (which held the heat flux constant), and at 21 minutes water circulation through the bladder at 17° C. was initiated with a commensurate increase in heat flux. At 30 minutes the negative pressure was set to zero causing an immediate drop in heat flux. At 36 minutes the negative pressure was reestablished to 40 mm Hg, and the heat flux immediately jumped back to and held at the maximum value. At 41 minutes the negative pressure was again removed, with the heat flux also falling to the previous lower value. This data demonstrates the mechanistic coupling between negative pressure and the enhancement of heat flow through the skin. This coupling appears to be driven by increased convection with blood flow through the negative pressure distended AVAs. The mechanistic action of negative pressure on heat transfer in the skin for the subject technology is verified by these data.

Example 4

Figure 21:
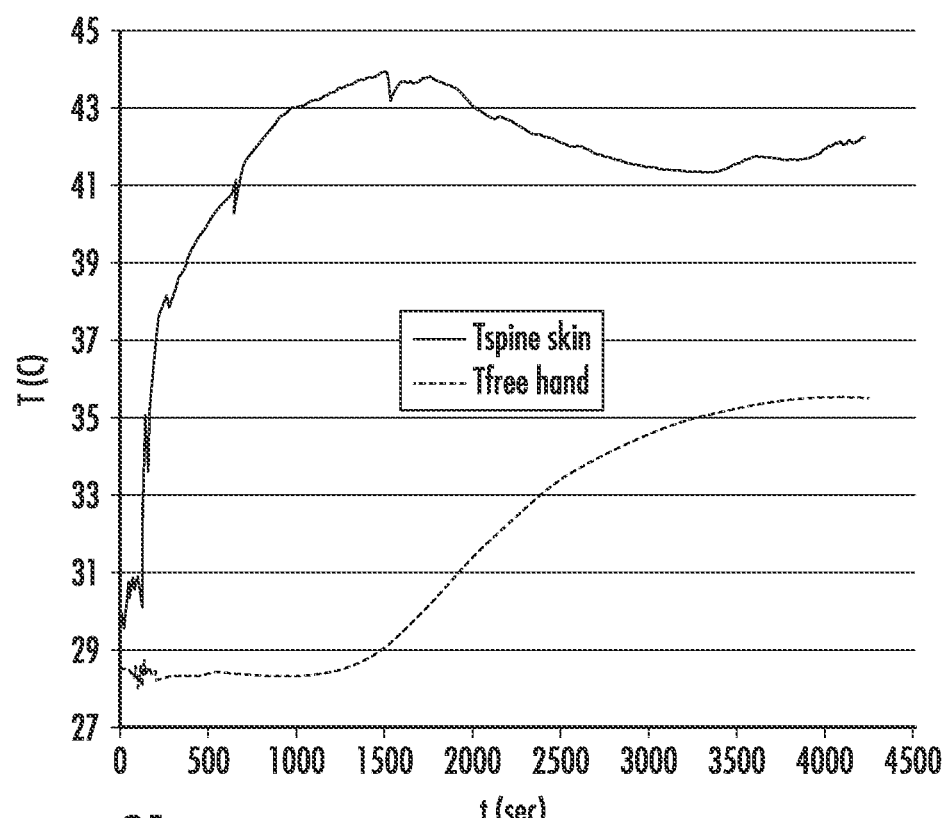
FIG. 21 is a graph illustrating temperature of spine skin and temperature of a hand over time.

Heating skin in a peripheral area rich in parasympathetic thermal sensors that effect AVA blood flow produces this result. The results are shown in FIG. 21. Heating the cervical spine of a subject was used to open vasoconstricted AVAs in glabrous skin of the hand of the subject which caused a large increase in blood perfusion, thereby warming the skin surface.

FIG. 21 shows example data for a test in which a strongly vasoconstricted state was relaxed by application of focal heating to a selected area along the spine. The total surface area heated was quite small to avoid a total heat load that could affect the core temperature. Core temperature was monitored continuously and remained constant through the process. A surface thermocouple was mounted on the palm of one hand when the subject was in a state of strong vasoconstriction that had existed for more than one hour prior to the experiment. A thermocouple was also mounted on the skin above the spine at the site where heating was applied.

The data show the trigger temperature for this effect is in a narrow range of above about 40° C. The temperature was restricted to below about 44° C. which is near the threshold for causing thermal injury. Thus, the temperature range was from about 40° C. to below about 44° C.

Application of heat to the skin of the cervical spine leads directly to AVA vasodilation in glabrous skin. The vasodilation produced enhanced perfusion of warm blood from the body core, convective heat transfer to the surrounding tissue, and warming of the surface of the skin as the heat diffuses away from the AVA vascular bed. The mechanistic action of peripheral heating on AVA vasodilation from the vasoconstricted state for the subject technology is verified by these data.

Example 5

Warming the Cervical Spine Increases Blood Flow in Vasoconstricted AVAs

The application of thermal stimulation via heating to specific peripheral areas of central thermoregulatory control cause a significant increase in the flow of blood through the AVA vascular structure and the associated retia venosa. A fiber optic laser Doppler flow probe was used to measure the change in blood flow in glabrous skin as a function of the magnitude of applied surface heating to the cervical spine. A surface filament thermocouple was used to measure the temperature of the skin on the surface at the cervical spine over which an electric heating pad was applied.

Figure 19:
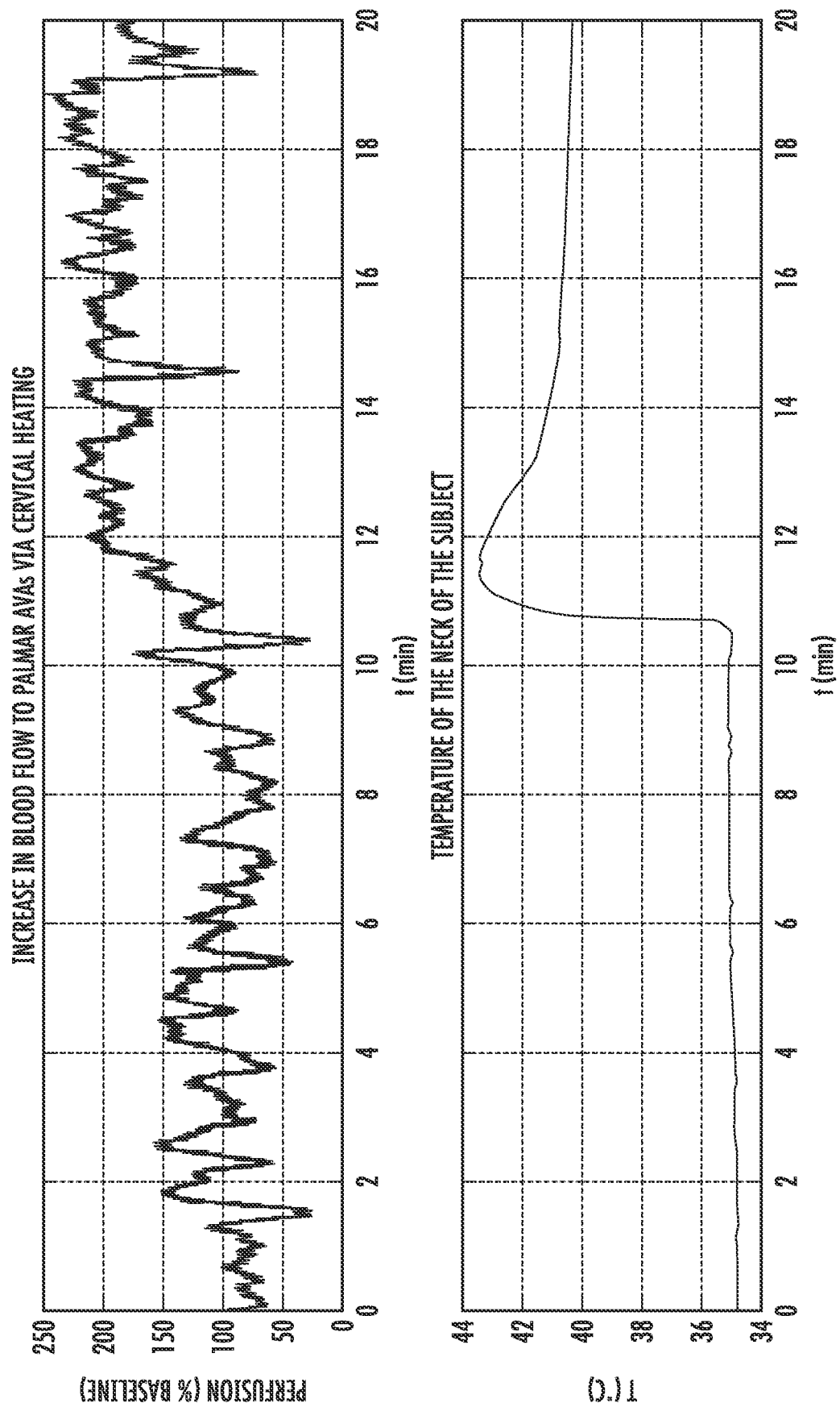
FIG. 19 illustrates graphs showing increase in blood flow to palmar arteriovenous anastomoses (AVAs) by cervical heating and temperature of the neck of a subject.
Figure 20:
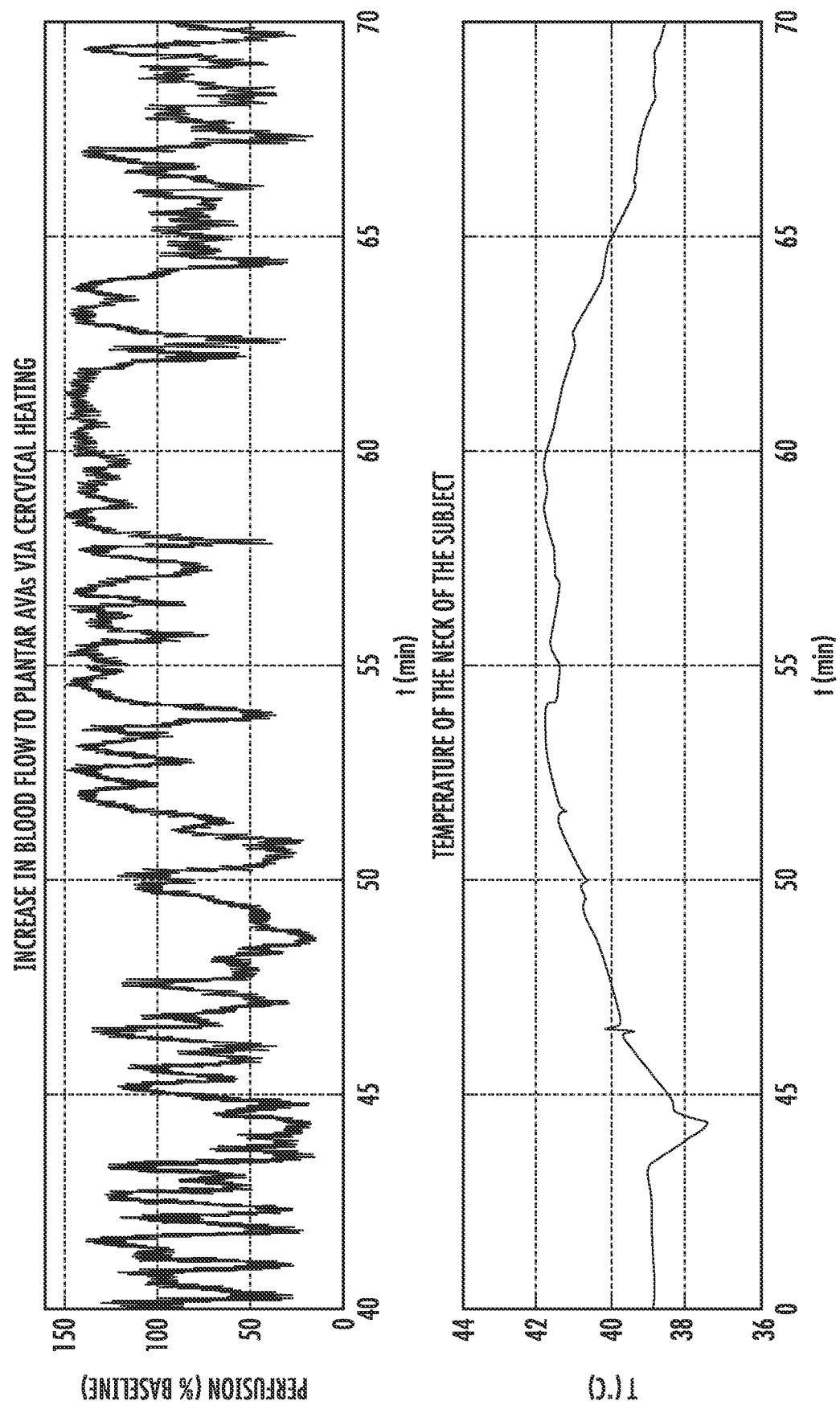
FIG. 20 illustrates graphs showing increase in blood flow to plantar arteriovenous anastomoses (AVAs) by cervical heating and temperature of the neck of a subject.

FIGS. 19 and 20 show the increase in flow of blood through the finger tip and second toe, respectively, in response to the application of heating on the skin surface at the cervical spine. The data show in both areas of glabrous skin a direct increment in perfusion following elevation of the skin temperature at the cervical spine.

Example 6

Warming the Cervical Spine Increases the Surface Temperature of Initially Vasoconstricted Palmar and Plantar Skin Heating skin in a peripheral area rich in parasympathetic thermal sensors produces an elevation in the temperature of glabrous skin when there is an initial state of vasoconstriction. Heating the cervical spine of a subject was used to open vasoconstricted AVAs in glabrous skin of the hand and foot of the subject which caused a large increase in blood perfusion, thereby warming the skin surface.

Figure 22:
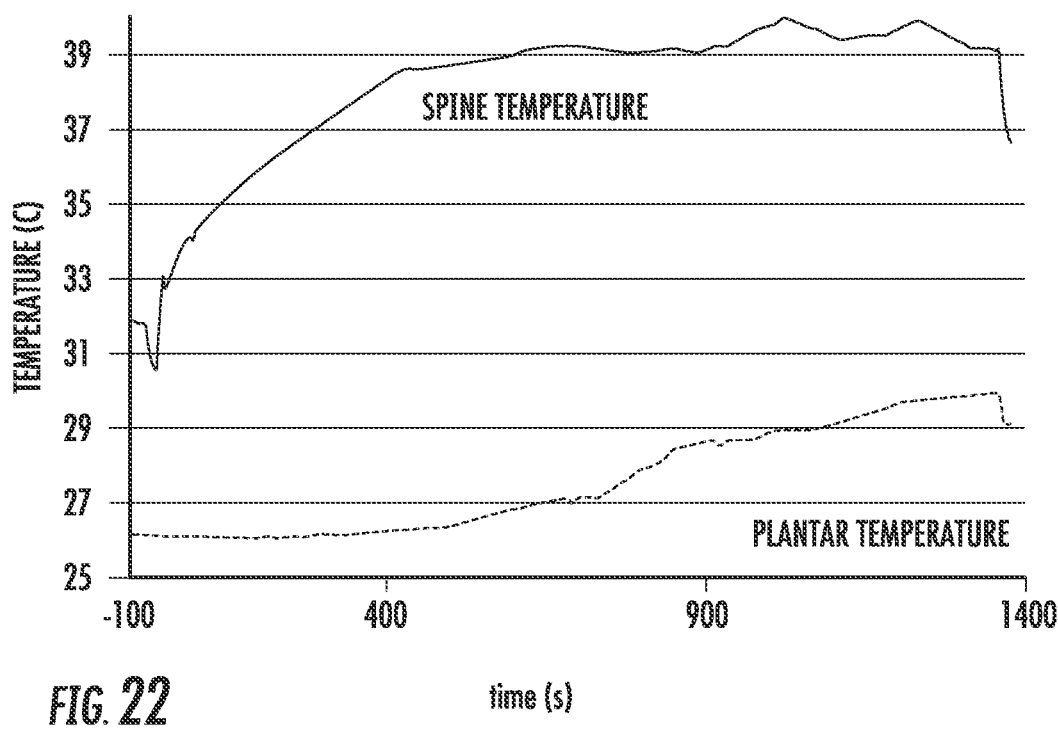
FIG. 22 is a graph illustrating temperature of spine skin and plantar temperature over time.

FIGS. 21 and 22 show example data for tests in which a strongly vasoconstricted state was relaxed by application of focal heating to a selected area along the spine. The total surface area heated was quite small to avoid a total heat load that could affect the core temperature. Core temperature was monitored continuously and remained constant through the process. A surface thermocouple was mounted on the palm of one hand, FIG. 21, or to the sole of one foot, FIG. 22, when the subject was in a state of strong vasoconstriction that had existed for more than one hour prior to the experiment. A thermocouple was also mounted on the skin above the spine at the site where heating was applied.

The data show the trigger temperature for this effect is in a narrow range of above about 39° C. on the surface. The temperature was restricted to below about 43° C., which is near the threshold for causing thermal injury. The effective temperature range for heating the skin surface over the cervical spine to trigger AVA vasodilation ranges from about 39° C. to below about 43° C.

Application of heat to the skin of the cervical spine leads directly to AVA vasodilation in glabrous skin. The vasodilation produced enhanced perfusion of warm blood from the body core, convective heat transfer to the surrounding tissue, and warming of the surface of the skin as the heat diffuses away from the AVA vascular bed. The mechanistic action of peripheral heating on AVA vasodilation from the vasoconstricted state for the subject technology is verified by these data.

Figure 23:
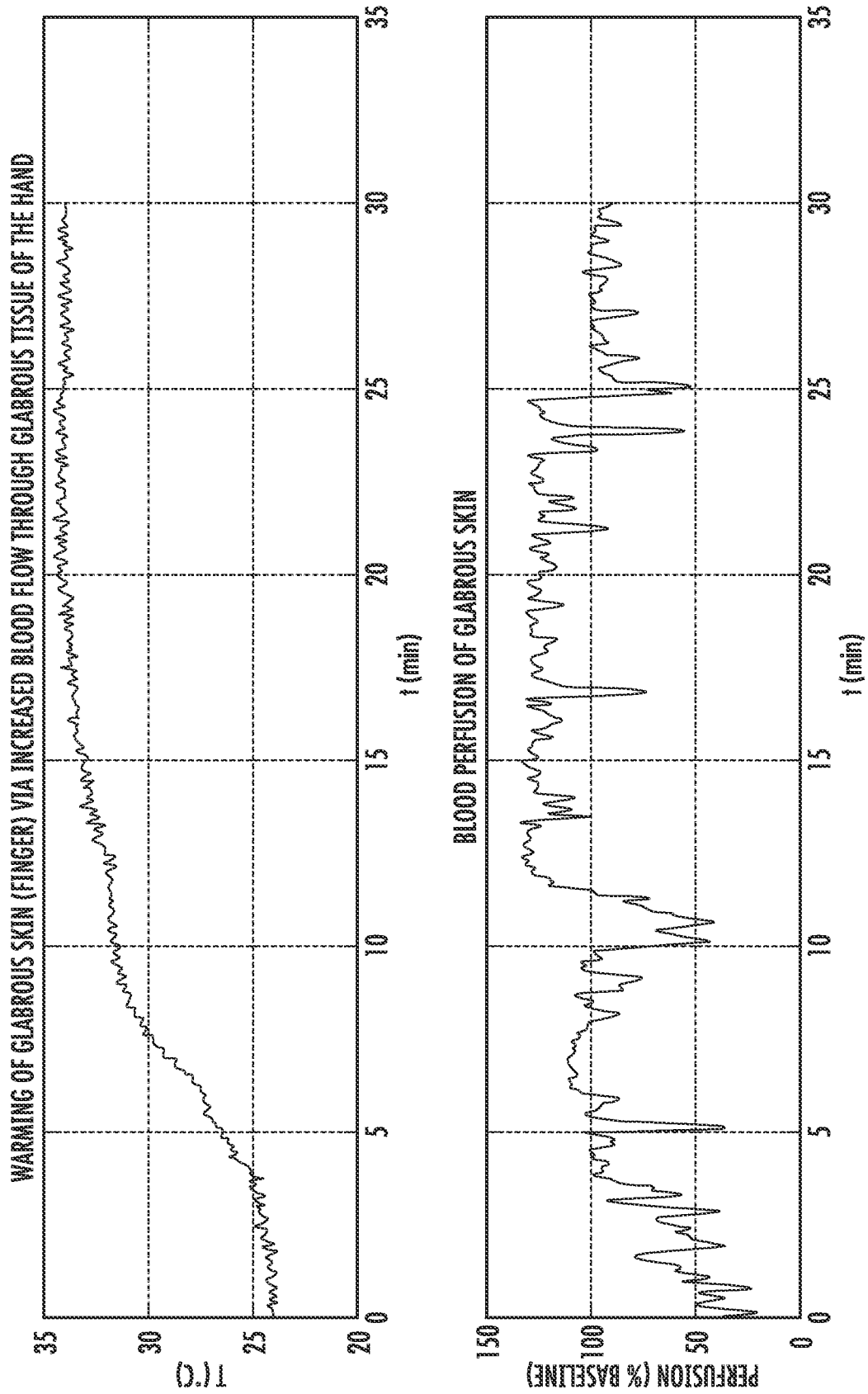
FIG. 23 illustrates graphs showing warming of glabrous skin via increased blood flow through glabrous tissues of the hand and blood perfusion of glabrous skin over time.

A fiber optic thermal probe was also used to measure the skin surface temperature at the site of perfusion measurement at the finger tip. FIG. 23 illustrates the temperature history during this experiment. Initial temperature of the skin was 24° C., which is indicative of a vasoconstricted state as is confirmed by the correspondingly low value of AVA perfusion. The data for the rate of perfusion through the AVAs shows a steady transition over the first 11 minutes to a vasodilated state, with a corresponding rise in the skin temperature by approximately 8° C. to a new equilibrium value as the increased flow of warm blood from the body core through the AVAs caused an interior convective source that translated to the progressive warming of the skin surface. These data show the coupling between AVA perfusion level and skin heat transfer. A further stimulation of blood perfusion at 11 minutes causes a greater convection effect between warm blood and the skin tissue, issuing in a further increment in surface temperature. FIG. 23 documents the further increment in surface temperature by 2° C. as a result of the application of negative pressure. The net increase in surface temperature of the skin was 10° C. as a result of the increase in AVA perfusion. The mechanistic action of blood perfusion on convective heat transfer in the glabrous skin is verified by these data.

Example 7

Warming the Cervical Spine in Conjunction with Cooling the Palmar or Plantar Skin Surfaces Causes a Reduction in Body Core Temperature For applications of the devices, systems and methods of the disclosure, from a starting state wherein the AVAs are vasoconstricted, a state of vasodilation is effected in order to realize the benefits of enhancement of cutaneous circulation. An example is the use of therapeutic hypothermia to treat a subject who is suffering an episode of brain ischemia that is caused, for example, by stroke, cardiac arrest, or traumatic brain injury. Such a subject may be in a state of AVA vasoconstriction. At this time, when therapeutic hypothermia is applied within a short time window of efficacy, according to the methods of the disclosure, a state of AVA vasodilatation is induced and maintained throughout the core cooling process.

The palmar surface of the hand and sometimes the plantar surface of the foot were subjected to cooling by contacting them with a bladder through which chilled water was circulated at the same time that heating was applied to the skin overlying the cervical spine. A heat flux gauge and thermocouple were affixed to the palm/sole of the foot in an area where it contacted the bladder. The protocol consisted of an equilibration period at room temperature, followed by bladder perfusion with water at 20° C.

Figure 24:
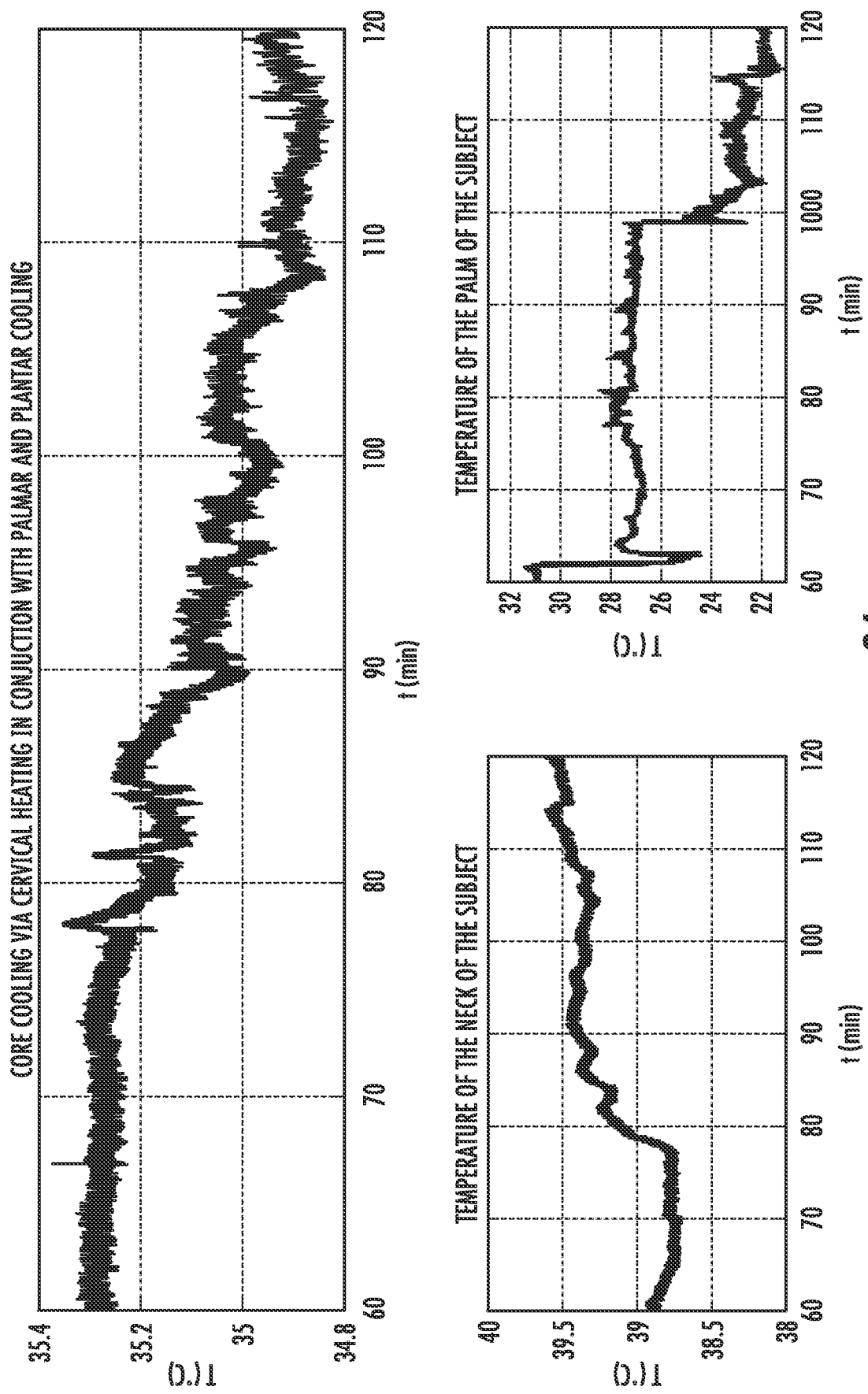
FIG. 24 illustrates graphs showing core cooling via cervical heating in conjunction with palmar and plantar cooling, the temperature of the neck over time and the temperature of the palm over time.

FIG. 24 shows data from these tests. After about the $80^{th}$ minute of the experiment, both neck heating and palmar cooling were in effect. Subsequently, in the 30 minute period roughly between the $80^{th}$ and $110^{th}$ minutes, the body core of the subject decreased about 0.4 degrees Celsius.

As used in the specification, and in the appended claims, the singular forms "a," "an," "the," include plural referents unless the context clearly dictates otherwise.

The term "comprising" and variations thereof as used herein are used synonymously with the term "including" and variations thereof and are open, non-limiting terms.

Many modifications and other embodiments of the invention set forth herein will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of cooling or maintaining a cooled core body temperature of a mammal subject, comprising:
   inducing and maintaining a condition of vasodilation in glabrous tissue of the subject, wherein the inducing and maintaining of vasodilation in the glabrous tissue does not include applying a mechanical force caused by application of pressure to the glabrous tissue of the subject sufficient to induce or maintain increased blood flow in the glabrous tissue; and
   applying a cooling stimulus using a cooling device localized to the glabrous tissue, to skin overlying the glabrous tissue, or both, during the maintenance of the vasodilation condition therein the glabrous tissue, wherein the localized cooling application cools blood in the vasodilated vasculature of the glabrous tissue, said cooled blood circulating to the subject's body core to cause cooling or maintenance of the subject's cooled core body temperature.

2. The method of claim 1, wherein the induction and maintenance of vasodilation is activated by localized heating of the subject's peripheral thermoregulatory control tissue located in the cervical or lumbar spine region of the subject.

3. The method of claim 1, wherein the induction and maintenance of vasodilation is a result of anesthesia.

* * * * *